(12) United States Patent
Gamelin et al.

(10) Patent No.: US 11,638,834 B2
(45) Date of Patent: May 2, 2023

(54) SYSTEMS AND METHODS FOR PHOTOTHERAPY CONTROL

(71) Applicant: ZERIGO HEALTH, INC., San Diego, CA (US)

(72) Inventors: Andre S. Gamelin, Vista, CA (US); Martyn C. Gross, San Diego, CA (US)

(73) Assignee: Zerigo Health, Inc., San Diego, CA (US)

( * ) Notice: Subject to any disclaimer, the term of this patent is extended or adjusted under 35 U.S.C. 154(b) by 283 days.

(21) Appl. No.: 15/747,100

(22) PCT Filed: Jul. 21, 2016

(86) PCT No.: PCT/US2016/043378
§ 371 (c)(1),
(2) Date: Jan. 23, 2018

(87) PCT Pub. No.: WO2017/019455
PCT Pub. Date: Feb. 2, 2017

(65) Prior Publication Data
US 2018/0369604 A1    Dec. 27, 2018

Related U.S. Application Data

(60) Provisional application No. 62/196,824, filed on Jul. 24, 2015.

(51) Int. Cl.
*A61N 5/06* (2006.01)
*A61B 34/10* (2016.01)

(52) U.S. Cl.
CPC ............ *A61N 5/0616* (2013.01); *A61B 34/10* (2016.02); *A61N 5/06* (2013.01);
(Continued)

(58) Field of Classification Search
CPC ................... A61N 5/0616; A61N 5/06; A61N 2005/0627; A61N 2005/0628;
(Continued)

(56) References Cited

U.S. PATENT DOCUMENTS 5,698,866 A    12/1997  Doiron et al.
5,720,772 A    2/1998   Eckhouse
(Continued)

FOREIGN PATENT DOCUMENTS

CA    2387071 A1    2/2002
CA    2452408 A1    1/2003
(Continued)

OTHER PUBLICATIONS

European Patent Application No. 15743284.0 Office Action dated Jun. 13, 2018.
(Continued)

*Primary Examiner* — Carl H Layno
*Assistant Examiner* — Michael J Lau
(74) *Attorney, Agent, or Firm* — Wilson Sonsini Goodrich & Rosati

(57) ABSTRACT

The present disclosure relates to systems, methods, and uses of systems for treating a skin condition with phototherapy. A system comprises (a) a phototherapy device comprising a phototherapy light source; (b) a patient computing device comprising a processor and a memory, the patient computing device configured to: transmit a first signal to the phototherapy device enabling operation of the phototherapy device according to one or more conditional prescription parameters, activate the phototherapy light source, and transmit a second signal reporting operation of the phototherapy device; and (c) a server configured to communicate with the patient computing device and receive the second signal. Also disclosed are systems, methods and composi-
(Continued)

tions for controlling phototherapy treatments of the skin comprising (a) incorporating sun exposure into a prescribed phototherapy treatment; (b) quantitative measurement of erythema using digital image processing; (c) computer aided guidance for administration of targeted phototherapy; (d) treatment recommendations from outcome based analytics of a population of connected phototherapy devices; (e) an emollient with UV fading dye to visibly identify treated areas in the administration of targeted phototherapy.

23 Claims, 11 Drawing Sheets

(52) U.S. Cl.
CPC ............... *A61N 2005/0627* (2013.01); *A61N 2005/0628* (2013.01); *A61N 2005/0645* (2013.01); *A61N 2005/0651* (2013.01); *A61N 2005/0657* (2013.01); *A61N 2005/0661* (2013.01)

(58) Field of Classification Search
CPC .... A61N 2005/0645; A61N 2005/0651; A61N 2005/0652; A61N 2005/0657; A61N 2005/0661; A61B 34/10
USPC .......................................................... 607/88
See application file for complete search history.

(56) References Cited

U.S. PATENT DOCUMENTS

| | | | |
|---|---|---|---|
| 5,836,999 | A | 11/1998 | Eckhouse et al. |
| 6,063,108 | A | 5/2000 | Salansky et al. |
| 6,290,713 | B1 | 9/2001 | Russell |
| 6,413,268 | B1 | 7/2002 | Hartman |
| 6,436,127 | B1 | 8/2002 | Anderson et al. |
| 6,663,659 | B2 | 12/2003 | McDaniel |
| 6,692,251 | B1 | 2/2004 | Logan et al. |
| 6,835,202 | B2 | 12/2004 | Harth et al. |
| 6,902,563 | B2 | 6/2005 | Wilkens et al. |
| 7,081,128 | B2 | 7/2006 | Hart et al. |
| 7,087,074 | B2 | 8/2006 | Hasegawa |
| 7,211,299 | B2 | 5/2007 | Siegel |
| 7,252,628 | B2 | 8/2007 | Van Hal et al. |
| 7,276,059 | B2 | 10/2007 | Irwin |
| H2242 | H | 7/2010 | Gonzales |
| 7,886,749 | B2 | 2/2011 | Irwin |
| 7,887,533 | B2 | 2/2011 | Barolet et al. |
| 7,921,853 | B2 | 4/2011 | Fiset |
| 7,985,219 | B2 | 7/2011 | Wilkens et al. |
| 8,157,807 | B2 | 4/2012 | Ferren et al. |
| 8,435,273 | B2 | 5/2013 | Lum et al. |
| 8,486,056 | B2 | 7/2013 | Irwin |
| 8,486,124 | B2 | 7/2013 | Hendrix et al. |
| 8,518,027 | B2 | 8/2013 | Weckwerth et al. |
| 8,518,094 | B2 | 8/2013 | Wang |
| 8,523,849 | B2 | 9/2013 | Liu et al. |
| 8,620,451 | B2 | 12/2013 | Kennedy |
| 8,801,254 | B2 | 8/2014 | McNeill et al. |
| 8,864,362 | B2 | 10/2014 | Sherman et al. |
| 9,901,747 | B2 | 2/2018 | Gamelin et al. |
| 9,913,993 | B2 | 3/2018 | Gross et al. |
| 2002/0022008 | A1 | 2/2002 | Forest et al. |
| 2002/0128695 | A1 | 9/2002 | Harth et al. |
| 2002/0182563 | A1 | 12/2002 | Boutoussov et al. |
| 2004/0034397 | A1 | 2/2004 | Lin |
| 2004/0054386 | A1 | 3/2004 | Martin et al. |
| 2004/0166249 | A1 | 8/2004 | Siegel |
| 2004/0188696 | A1 | 9/2004 | Hsing et al. |
| 2005/0143793 | A1 | 6/2005 | Korman et al. |
| 2005/0157515 | A1 | 7/2005 | Chen et al. |
| 2005/0177208 | A1* | 8/2005 | Irwin ................... A61N 5/0603 607/94 |
| 2005/0196720 | A1 | 9/2005 | Ostler et al. |
| 2005/0206518 | A1 | 9/2005 | Welch et al. |
| 2006/0085053 | A1* | 4/2006 | Anderson ............... A61B 5/444 607/94 |
| 2006/0106435 | A1* | 5/2006 | Fraval .................. A61B 5/0059 607/88 |
| 2006/0289887 | A1 | 12/2006 | Bui et al. |
| 2007/0049996 | A1* | 3/2007 | Black ................... A61B 18/203 607/89 |
| 2007/0078501 | A1 | 4/2007 | Altshuler et al. |
| 2007/0198004 | A1 | 8/2007 | Altshuler et al. |
| 2007/0276455 | A1 | 11/2007 | Fiset |
| 2008/0027518 | A1 | 1/2008 | Island et al. |
| 2009/0221999 | A1* | 9/2009 | Shahidi .................. A61B 34/10 128/898 |
| 2009/0240310 | A1 | 9/2009 | Kennedy |
| 2009/0254154 | A1* | 10/2009 | De Taboada ......... A61N 5/0613 607/110 |
| 2010/0069898 | A1 | 3/2010 | O'Neil et al. |
| 2010/0076529 | A1* | 3/2010 | Tucker ................ A61N 5/0616 607/90 |
| 2010/0127299 | A1 | 5/2010 | Smith et al. |
| 2010/0145419 | A1* | 6/2010 | Fraval ................... A61N 5/062 607/94 |
| 2010/0196343 | A1* | 8/2010 | O'Neil ................... A61Q 19/10 424/94.4 |
| 2011/0034971 | A1* | 2/2011 | Svanberg ............. A61N 5/0601 607/88 |
| 2011/0037002 | A1 | 2/2011 | Johnson et al. |
| 2011/0037844 | A1* | 2/2011 | Johnson ............... A61N 5/0613 348/E5.085 |
| 2011/0125229 | A1 | 5/2011 | Lytle et al. |
| 2011/0144410 | A1* | 6/2011 | Kennedy ............... A61N 5/0616 600/2 |
| 2011/0190579 | A1 | 8/2011 | Ziarno et al. |
| 2012/0022618 | A1 | 1/2012 | Lum et al. |
| 2012/0059441 | A1* | 3/2012 | Chang .................. A61N 5/0616 607/90 |
| 2012/0065493 | A1* | 3/2012 | Gertner ................ A61N 5/0622 604/23 |
| 2012/0078329 | A1 | 3/2012 | Shimada |
| 2012/0116485 | A1 | 5/2012 | Burgmann |
| 2012/0165907 | A1 | 6/2012 | Wagenaar et al. |
| 2012/0191162 | A1 | 7/2012 | Villa |
| 2012/0212960 | A1 | 8/2012 | Rodriguez |
| 2012/0222618 | A1 | 9/2012 | Olsen et al. |
| 2013/0013032 | A1 | 1/2013 | Irwin |
| 2013/0030264 | A1 | 1/2013 | Gopalakrishnan et al. |
| 2013/0066404 | A1* | 3/2013 | Tapper ................. A61N 5/0616 607/90 |
| 2013/0115180 | A1 | 5/2013 | Goren et al. |
| 2013/0144364 | A1 | 6/2013 | Wagenaar et al. |
| 2013/0172963 | A1 | 7/2013 | Moffat |
| 2013/0190841 | A1 | 7/2013 | McMillan |
| 2013/0231720 | A1* | 9/2013 | Luellau ................ A61N 5/0613 607/88 |
| 2013/0245417 | A1 | 9/2013 | Spector |
| 2013/0245724 | A1 | 9/2013 | Kaufman |
| 2013/0282080 | A1 | 10/2013 | Hendrix et al. |
| 2013/0301034 | A1* | 11/2013 | Olds ..................... H05B 47/11 356/218 |
| 2013/0317574 | A1 | 11/2013 | Gourgouliatos et al. |
| 2013/0345687 | A1 | 12/2013 | McMillan et al. |
| 2014/0031906 | A1 | 1/2014 | Brezinski |
| 2014/0039473 | A1* | 2/2014 | Liu ....................... A61N 5/0616 606/9 |
| 2014/0052223 | A1 | 2/2014 | Toepfer |
| 2014/0157174 | A1* | 6/2014 | Deroberts ............. G06F 3/0484 715/771 |
| 2014/0194957 | A1* | 7/2014 | Rubinfeld ............. A61F 9/0079 607/90 |
| 2014/0244292 | A1 | 8/2014 | Rosenberg et al. |
| 2014/0277299 | A1* | 9/2014 | Intintoli ............... A61N 5/0616 607/94 |
| 2014/0288351 | A1 | 9/2014 | Jones |
| 2014/0303547 | A1* | 10/2014 | Loupis ................ A61N 5/0624 604/20 |

(56) References Cited

U.S. PATENT DOCUMENTS

| | | |
|---|---|---|
| 2015/0022093 A1 | 1/2015 | Smith et al. |
| 2015/0025601 A1 | 1/2015 | Fiset |
| 2015/0025602 A1 | 1/2015 | Wagenaar et al. |
| 2015/0070188 A1 | 3/2015 | Aramburu |
| 2015/0165229 A1 | 6/2015 | Rodrigues |
| 2015/0177059 A1 | 6/2015 | Lian et al. |
| 2015/0217130 A1 | 8/2015 | Gross et al. |
| 2015/0230863 A1 | 8/2015 | Youngquist et al. |
| 2017/0056686 A1 | 3/2017 | Gamelin et al. |
| 2018/0319667 A1 | 11/2018 | Kaner et al. |
| 2021/0178181 A1 | 6/2021 | Gross et al. |
| 2021/0187317 A1 | 6/2021 | Gamelin et al. |

FOREIGN PATENT DOCUMENTS

| | | | |
|---|---|---|---|
| CA | 2767594 A1 | 1/2011 | |
| CA | 2861620 A1 | 7/2013 | |
| CN | 1578688 A | 2/2005 | |
| CN | 1728971 A | 2/2006 | |
| CN | 1250302 C | 4/2006 | |
| CN | 102006833 A | 4/2011 | |
| CN | 102481456 A | 5/2012 | |
| CN | ON-102470252 A | 5/2012 | |
| CN | 102811766 A | 12/2012 | |
| CN | 102870020 A | 1/2013 | |
| CN | 104168953 A | 11/2014 | |
| CN | 104640602 A | 5/2015 | |
| EP | 1307261 A1 | 5/2003 | |
| EP | 1575436 A1 | 9/2005 | |
| EP | 2252229 A1 | 11/2010 | |
| EP | 2258301 A2 | 12/2010 | |
| EP | 2445586 A1 | 5/2012 | |
| EP | 2448635 A2 | 5/2012 | |
| EP | 2451528 A1 | 5/2012 | |
| EP | 2494389 A2 | 9/2012 | |
| EP | 2670334 A1 | 12/2013 | |
| EP | 2800605 A1 | 11/2014 | |
| EP | 2877243 A1 | 6/2015 | |
| EP | 3280342 A1 | 2/2018 | |
| JP | 2002514481 A | 5/2002 | |
| JP | 2005534201 A | 11/2005 | |
| JP | 2006252506 A | 9/2006 | |
| JP | 2007510466 A | 4/2007 | |
| JP | 2008528188 A | 7/2008 | |
| JP | 2008539808 A | 11/2008 | |
| JP | 2009532079 A | 9/2009 | |
| JP | 2012502696 A | 2/2012 | |
| JP | 2012090950 A | 5/2012 | |
| JP | 2012531938 A | 12/2012 | |
| KR | 101349157 B1 | 1/2014 | |
| WO | WO-9958195 A1 | 11/1999 | |
| WO | WO-0114012 A1 | 3/2001 | |
| WO | WO-0213905 A1 | 2/2002 | |
| WO | WO-03001984 A2 | 1/2003 | |
| WO | WO-2004011848 A2 | 2/2004 | |
| WO | WO-2004054458 A1 | 7/2004 | |
| WO | WO-2005046793 A2 | 5/2005 | |
| WO | WO-2006081312 A2 | 8/2006 | |
| WO | WO-2006099413 A2 | 9/2006 | |
| WO | WO-2008061197 A2 | 5/2008 | |
| WO | WO-2009113986 A1 | 9/2009 | |
| WO | WO-2010010321 A1 | 1/2010 | |
| WO | WO-2010033630 A1 | 3/2010 | |
| WO | WO-2010150165 A1 | 12/2010 | |
| WO | WO-2011001344 A2 | 1/2011 | |
| WO | WO-2011004170 A1 | 1/2011 | |
| WO | WO-2011053804 A2 | 5/2011 | |
| WO | WO-2011109628 A1 | 9/2011 | |
| WO | WO-2012106689 A1 | 8/2012 | |
| WO | WO-2013020179 A1 | 2/2013 | |
| WO | WO-2013103743 A1 | 7/2013 | |
| WO | WO-2013138517 A1 | 9/2013 | |
| WO | WO-2014013386 A1 | 1/2014 | |
| WO | WO-2014018103 A1 | 1/2014 | |
| WO | WO-2014040177 A1 | 3/2014 | |
| WO | WO-2014054458 A1 | 4/2014 | |
| WO | WO-2014076503 A1 | 5/2014 | |
| WO | WO-2014131115 A1 | 9/2014 | |
| WO | WO-2014162271 A2 * | 10/2014 | ........... A61N 5/0618 |
| WO | WO-2015041919 A1 | 3/2015 | |
| WO | WO-2015117159 A1 | 8/2015 | |
| WO | WO-2016164228 A1 | 10/2016 | |
| WO | WO-2017019455 A2 | 2/2017 | |

OTHER PUBLICATIONS

Japanese Patent Application No. 2016-567480 First office Action dated Apr. 2, 2018.
Asztalos et al., The impact of emollients on phototherapy: A review. Journal of the American Academy of Dermatology, 68(5):817-824, 2013.
European Patent Application No. 15743284.0 extended European Search Report dated Sep. 5, 2017.
PCT/US2015/014327 International Preliminary Report on Patentability dated Mar. 31, 2016.
PCT/US2015/014327 International Search Report and Written Opinion dated May 7, 2015.
PCT/US2016/043378 International Search Report and Written Opinion dated Jan. 26, 2017.
U.S. Appl. No. 14/613,297 Office Action dated Feb. 8, 2017.
U.S. Appl. No. 14/613,297 Office Action dated Jul. 11, 2017.
U.S. Appl. No. 14/613,297 Office Action dated Nov. 6, 2017.
Yarbrough et al., Continued use of home narrowband ultraviolet B light phototherapy for psoriasis after completion of a clinical trial. Journal of American Academy of Dermatology, 60(5):877-879, 2009.
European Patent Application No. 15831098.5 European Search Report dated Mar. 4, 2019.
Japanese Patent Application No. 2017-548298 Office Action dated Mar. 23, 2020.
PCT Patent Application No. PCT/US2016/024996 International Search Report and Written Opinion dated Jul. 1, 2016.
PCT/US2016/024996 International Preliminary Report on Patentability dated Oct. 10, 2017.
U.S. Appl. No. 15/351,119 Office Action dated Aug. 28, 2017.
U.S. Appl. No. 15/351,119 Office Action dated Feb. 23, 2017.
U.S. Appl. No. 15/839,678 Office Action dated Apr. 1, 2019.
U.S. Appl. No. 15/839,678 Office Action dated Dec. 31, 2019.
U.S. Appl. No. 15/881,422 Office Action dated Jan. 16, 2020.
European Patent Application No. 20187070.6 European Search Report dated Jan. 26, 2021.
U.S. Appl. No. 15/839,678 Office Action dated Sep. 4, 2020.
U.S. Appl. No. 15/881,422 Final Office Action dated Aug. 4, 2020.
U.S. Appl. No. 17/166,872 Office Action dated Sep. 16, 2022.

* cited by examiner

Step 1: Identify area to be treated

Step 2: Apply composition to area

Step 3: Treat first targeted area with UV

Step 4: Complete treatment using faded areas as guide

Step 5: Expose area to ambient UV

SYSTEMS AND METHODS FOR PHOTOTHERAPY CONTROL

This application is filed pursuant to 35 U.S.C. § 371 as a United States National Phase Application of International Application No. PCT/US2016/043378 entitled "SYSTEMS AND METHODS FOR PHOTOTHERAPY CONTROL" filed Jul. 21, 2016, which claims the benefit of U.S. Provisional Application No. 62/196,824 filed on Jul. 24, 2015, each of which contents are hereby incorporated by reference in its entirety.

BACKGROUND

Psoriasis is a common relapsing remitting skin condition that affects roughly 2-4% of the general population. Psoriasis is characterized by red, scaly, itchy skin lesions that may occur anywhere on the body. The causes of psoriasis are not well understood, but it is generally believed to be a genetic disease.

The general pathogenesis psoriasis is immune mediated. Immune cells incorrectly identify normal skin cells as pathogenic, and send out cell signals that cause the production of new skin cells. The overgrown skin cells comprise the psoriasis lesions.

No cure currently exists for psoriasis, and it is difficult to treat in part because of its chronically recurring and remitting nature.

Vitiligo is a skin condition in which there is a loss of brown color (pigment) from areas of skin, resulting in irregular white patches that feel like normal skin.

Eczema is a term for several different types of skin swelling.

SUMMARY

In a first broad embodiment, the present disclosure provides a system for treating a patient with phototherapy. In a certain embodiment, the patient is affected with a skin condition. The system includes a phototherapy device comprising a phototherapy light source and a patient computing device comprising a processor and a memory. The patient computing device is configured to: transmit a first signal to the phototherapy device enabling operation of the phototherapy device according to one or more conditional prescription parameters, activate the phototherapy light source, and transmit a second signal reporting operation of the phototherapy device. The system also includes a server configured to communicate with the patient computing device and receive the second signal.

In some embodiments, the system also includes a remote computing device configured to communicate with the server, the remote computing device including a processor and a memory, the remote computing device being configured to present a graphic user interface allowing a health care provider to set the one or more conditional prescription parameters, review information pertaining to operation of the phototherapy device, and adjust the one or more conditional prescription parameters, transmit a first communication to the server, and receive a second communication from the server.

In some embodiments, the conditional prescription parameters include one or more of: number and location of treatment sites, initial dose, method to determine subsequent doses, method to determine adjustments for missed days, maintenance treatment dose, treatment assessment method, treatment assessment frequency, treatment parameters in case the patient computing device is unavailable, enablement of the treatment dependent on completion of office visits or consults, enablement of the device dependent on acknowledgement of physician supplied materials, enablement of the device dependent on fulfillment of other physician requests such as user supplied photos, conditions in which the treatment would be disabled, or combinations thereof.

In some embodiments, the server comprises a database of patient records and prescribed treatment protocols comprising conditional prescription parameters.

In some embodiments, the patient records comprise: treatment dates and times, treatment durations, applied treatment energies, treatment site photos, analysis of treatments site photos, patient/physician correspondence, assessments of treatment sites, changes to the treatment protocol, and/or a combination thereof.

In some embodiments, the server is configured to perform analysis of patient records, prescribed treatment protocols, and outcomes over populations of patients.

In some embodiments, the server is further configured to perform computational analysis. In some embodiments, the computational analysis comprises an analysis of degree of erythema of a treated area of skin and surrounding skin tissue. In some embodiments, the computational analysis comprises an analysis of treatment progression comprising size and severity of the skin condition or of a disease.

In an embodiment, the server is further configured to determine an initial phototherapy dose based on a user skin type or susceptibility to erythema of a user of the phototherapy device.

In an embodiment, the phototherapy device comprises a hand-held phototherapy device. In some embodiments, the phototherapy light source is configured to emit a light comprising a UVB wavelength in the range of 300-320 nm. In some embodiments, the phototherapy light source comprises a light emitting diode (LED).

In some embodiments, the computing device comprises a smartphone, the signals comprise wireless signals, the transmitter comprises a wireless transmitter, and the receiver comprises a wireless receiver.

In some embodiments, the computing device is further configured to present an interface allowing the user to capture an image of a treated area of skin and the surrounding skin tissue. In some embodiments, the computing device is further configured to present an interface providing guidance to the user for operation of the phototherapy device. In some embodiments, the computing device comprises a smartphone. In some embodiments, the patient computing device is further configured to present an interface providing a treatment schedule, treatment reminders, directions for how to use the phototherapy device, or any combination thereof.

In some embodiments, the skin condition comprises psoriasis, vitiligo, or eczema.

In a second broad embodiment, the present disclosure provides use of the phototherapy system(s) as described herein for treating a skin condition with phototherapy.

In a third broad embodiment, the present disclosure provides a method for treating a skin condition with phototherapy, including: transmitting, by a patient computing device, a first signal to a phototherapy device comprising a phototherapy light source, the first signal enabling operation of the phototherapy device according to one or more conditional prescription parameters; activating, by the patient computing device, the phototherapy light source; transmitting, by the patient computing device, a second signal; and receiving, by a server, the second signal, the server being configured to communicate with the patient computing device.

In some embodiments, the method includes transmitting, by a remote computing device, a first communication to the server; and receiving, by the remote computing device, a second communication from the server.

In some embodiments, the method includes further comprising transmitting the first communication from the server to the patient computing device and receiving by the patient computing device the first communication. In some embodiments, the first communication enables the patient computing device to transmit the first signal.

In some embodiments, the server stores patient records. In some embodiments, the patient records comprise: treatment dates and times, treatment durations, applied treatment energies, treatment site photos, analysis of treatments site photos, patient/physician correspondence, assessments of treatment sites, changes to the treatment protocol, or any combination thereof.

In some embodiments, the methods include performing, by the server, image analysis of an image of an area of skin affected by a skin condition and/or surrounding skin tissue. In some embodiments, the image analysis comprises an analysis of degree of erythema of an area of skin affected by the skin condition and/or the surrounding skin tissue. In some embodiments, the image analysis comprises an analysis of treatment progression comprising size and severity of disease.

In some embodiments, the method comprises a step of determining, by the server, a subsequent phototherapy dose based on a skin type or susceptibility to erythema of a user of the phototherapy device.

In some embodiments, the phototherapy device comprises a hand-held phototherapy device. In some embodiments, the phototherapy light source is configured to emit a light comprising a UVB wavelength in the range of 300-320 nm. In some embodiments, the phototherapy light source comprises a light emitting diode (LED).

In some embodiments, the patient computing device comprises a smartphone and the signals comprise wireless signals.

In some embodiments, the method further comprises displaying, by the patient computing device, a treatment schedule, treatment reminders, directions for how to use the phototherapy device, or any combination thereof.

In some embodiments, the skin condition comprises psoriasis, eczema, or vitiligo.

In a fourth broad embodiment, the present disclosure provides a system for treating a skin condition, the condition comprising psoriasis, vitiligo, or eczema, with phototherapy, the system comprising a hand-held phototherapy device comprising a light emitting diode (LED) phototherapy light source configured to emit a light comprising a UVB wavelength in the range of 300-320 nm and a signal receiver; and a patient computing device comprising a smartphone, the smartphone comprising a processor and a memory, the smartphone configured to: present an interface providing a treatment schedule, treatment reminders, and directions for how to use the phototherapy device; transmit a first signal to the hand-held phototherapy device enabling operation of the phototherapy device according to one or more conditional prescription parameters originating at a remote computing device; activate the phototherapy light source; and transmit a second signal to a server; a server configured to: perform analysis of patient records, prescribed treatment protocols, and outcomes over populations of patients; perform computational analysis; determine an initial phototherapy dose based on a skin type or susceptibility to erythema of a user; and determine subsequent phototherapy doses using image analysis of an image of a treated area of skin and surrounding skin tissue, the analysis comprising an analysis of a degree of erythema of the treated area of skin or the surrounding tissue; a database communicatively connected to the server, the database storing patient records and prescribed treatment protocols; and a remote computing device configured to communicate with the server, the remote computing device comprising a processor and a memory, the remote computing device configured to: display a graphic user interface allowing a health care provider to enter the one or more conditional prescription parameters; transmit a first communication to the server; and receive a second communication from the server.

In a fifth broad embodiment, the present disclosure provides use of a system for treating a skin condition, the condition comprising psoriasis, vitiligo, or eczema, with phototherapy, the system comprising a hand-held phototherapy device comprising a light emitting diode (LED) phototherapy light source configured to emit a light comprising a UVB wavelength in the range of 300-320 nm and a signal receiver; and a patient computing device comprising a smartphone, the smartphone comprising a processor and a memory, the smartphone configured to: present an interface providing a treatment schedule, treatment reminders, and directions for how to use the phototherapy device; transmit a first signal to the hand-held phototherapy device enabling operation of the phototherapy device according to one or more conditional prescription parameters originating at a remote computing device; activate the phototherapy light source; and transmit a second signal to a server; a server configured to: perform analysis of patient records, prescribed treatment protocols, and outcomes over populations of patients; perform computational analysis; determine an initial phototherapy dose based on a skin type or susceptibility to erythema of a user; and determine subsequent phototherapy doses using image analysis of an image of a treated area of skin and surrounding skin tissue, the analysis comprising an analysis of a degree of erythema of the treated area of skin or the surrounding tissue; a database communicatively connected to the server, the database storing patient records and prescribed treatment protocols; and a remote computing device configured to communicate with the server, the remote computing device comprising a processor and a memory, the remote computing device configured to: display a graphic user interface allowing a health care provider to enter the one or more conditional prescription parameters; transmit a first communication to the server; and receive a second communication from the server.

In another embodiment, the disclosure provides a method to estimate or measure therapeutic UV exposure to the sun to fulfill treatment needs or to supplement a prescribed phototherapy treatment comprising: measuring or estimating UV exposure received by an individual; communicating UV exposure information to a computing device; and comparing the UV exposure to the prescribed phototherapy treatment. In certain embodiments, the UV exposure is estimated based on the location and duration of sun exposure using the broadcasted UV index for the nearest location. In certain embodiments, the sun exposure is determined using a wearable sensor that calculates the duration and time of day of sun exposure. In certain embodiments, the sun exposure is determined by manually recording the start time and stop time on a computing device. In certain embodiments, the location is determined by a GPS system connected to a computing device. In certain embodiments, the therapeutic UV exposure is measured by a calibrated photo sensor in proximity to the treatment site during exposure. In certain embodiments, the method further comprises predicting sun exposure required to reach a therapeutic target using at least one of the following: UV index forecast, measured therapeutic radiation, time of day, time of year, location and results from previous sessions. In certain embodiments, the method further comprises utilizing the exposure level to provide therapeutic treatment records. In certain embodiments, the method further comprises reducing a prescribed dose of a UV phototherapy device based on UV exposure from sunlight. In certain embodiments, the method further comprises adjusting the measured or estimated exposure with a scaling factor to account for differences from angle of incidence, shading, sunscreen, clothing coverage or other factors. In certain embodiments, the method further comprises monitoring the exposure level and communicating with the user using audio and/or visual information in order to ensure that the user does not exceed the target dose.

In another embodiment, the disclosure provides a method to determine the erythema level of unaffected skin within a treatment area comprising: taking a photographic image of the treatment area and surrounding skin; pre-processing the image to remove non-skin background areas; identifying the treated and untreated regions, by using image processing techniques such as boundary shape identification; computing the red color difference between skin on either side of the boundary; and comparing the red color difference to threshold values to determine whether unaffected skin is normal, pink or red.

In another embodiment, the disclosure provides a method to guide a targeted phototherapy treatment sequence comprising: communicating between a phototherapy device and a computing device to synchronize a phototherapy sequence plan to be administered; communicating information from the phototherapy device to the computing device during treatment, providing current status of the treatment sequence using audio or visual cues; communicating from the phototherapy device to the computing device when a treatment has been completed, or was interrupted; and communicating the next treatment location to the administrator on the computing device using audio or visual cues. In certain embodiments, the information communicated to the computing device includes current treatment location and time remaining on treatment. In certain embodiments, the computing device is a mobile phone. In certain embodiments, the phototherapy device communicates with the computing device wirelessly.

In another embodiment, the disclosure provides a method to develop evidence-based treatment recommendations from a connected system of phototherapy devices comprising: collecting outcomes of phototherapy treatments from a plurality of patients using phototherapy devices on the connected system; determining patient criteria of interest such as disease type, severity, age, skin type, years with disease, treatment area locations, geographical location, comorbidities, lifestyle, medical history; determining treatment criteria of interest such as dose control method, treatment frequency, missed treatments, dose levels, treatment history, other medications; correlating patient criteria and treatment criteria to positive outcomes and negative outcomes; and providing evidence based recommendations on treatment plan adjustments for an individual based on correlation evidence.

In another embodiment, the disclosure provides a composition for application to a region of a patient's skin including an area of a skin affected by a skin condition, in association with application of UV light to the affected area of skin for UV phototherapeutic treatment of the skin condition, the composition comprising: an emollient base for facilitating the absorbance of the applied UV light into the affected area of skin; and a UV-fading dye, the UV-fading dye present in the composition in a concentration suitable for temporarily staining the patient's skin upon application of the composition to the patient's skin, and for fading upon exposure to the applied UV light, thereby indicating where the UV light has been applied to the patient's skin. In certain embodiments, the emollient base is mineral oil. In certain embodiments, the UV-fading dye is present in the composition in a concentration suitable for: temporarily staining the patient's skin upon application of the composition to the patient's skin; fading upon exposure to the applied UV light, thereby indicating where the UV light has been applied to the patient's skin; and fading upon exposure to ambient sunlight conditions. In certain embodiments, the skin condition is psoriasis, eczema, vitiligo, or any combination thereof. In certain embodiments, the composition has an index of refraction of approximately 1.55. In certain embodiments, the UV fading dye fades upon exposure to ambient sunlight conditions after at least 15 minutes of ambient indoor lighting, and wherein the UV fading dye would not fade under ambient indoor conditions during a treatment session, absent administration of phototherapy with a phototherapy device, and no more than 30 minutes of ambient outdoor direct sunlight, and wherein excess dye would fade under ambient outdoor conditions. In certain embodiments, the UV-fading dye is present in the composition in a concentration suitable for fading upon exposure to UV radiation equal to or less than a dose of UV radiation received during a first time period, for example a first 2, 3, 4, 5, 10, or 30 seconds of phototherapy treatment with a phototherapy device.

In certain embodiments, disclosed herein is a method of indicating whether a region of a patient's skin containing an area of skin affected by a skin condition has been exposed to UV light in association with UV phototherapy treatment, the method comprising: applying a composition to the region of the patient's skin, the composition comprising: an emollient having an index of refraction of approximately 1.55 for facilitating absorbance of UV light into the affected area of skin; and a UV-fading dye, the UV-fading dye present in the composition in an concentration suitable for temporarily staining the patient's skin upon application of the composition to the patient's skin, and for fading upon exposure to UV light; administering UV light to the patient's skin affected by a skin condition in an amount suitable for providing a phototherapeutic effect to the affected skin; and observing where on the region of the patient's skin the UV-fading dye has faded, thereby determining where the UV light has been administered to the patient's skin.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
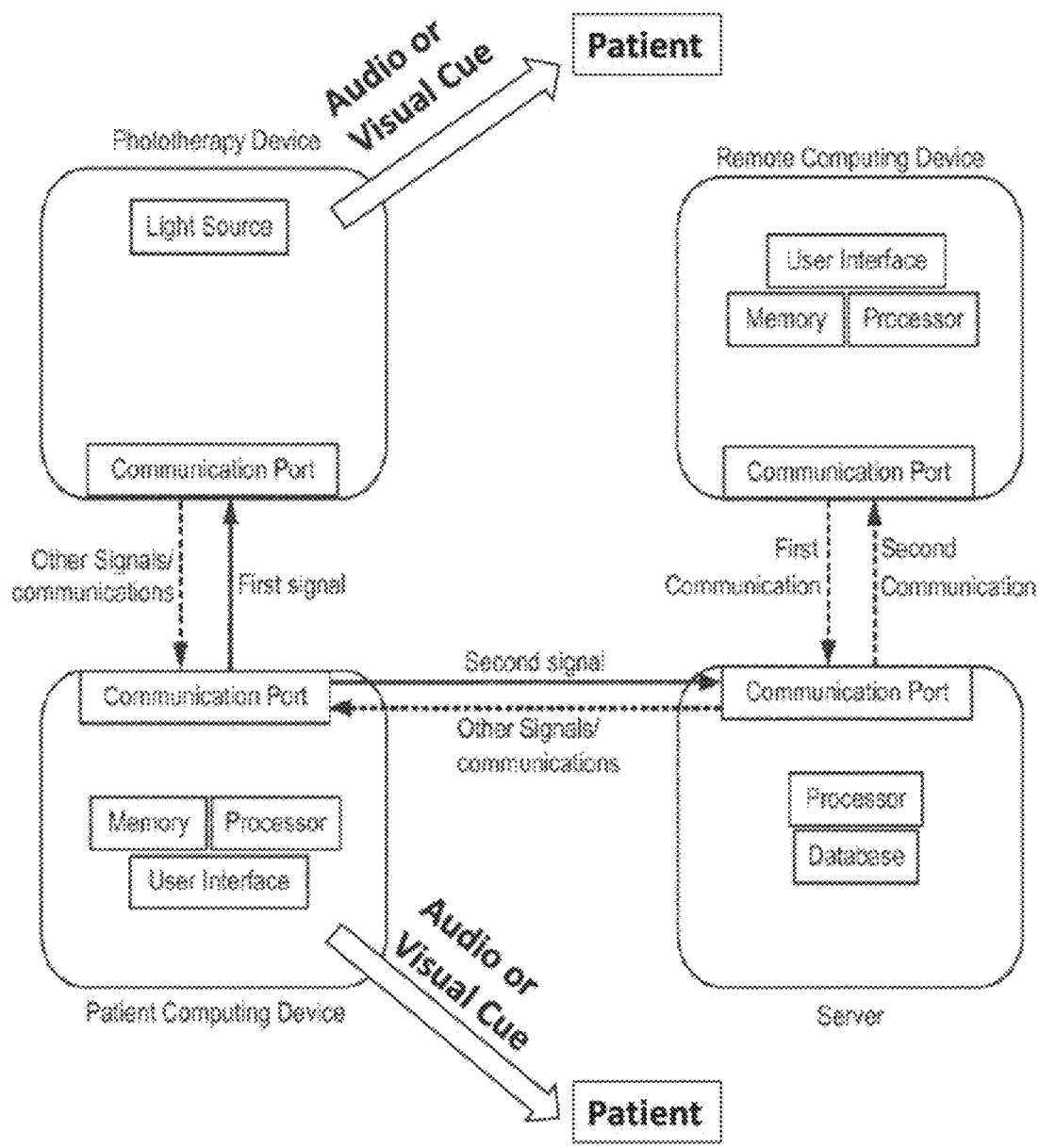
FIG. 1 illustrates a flow-chart showing a non-limiting example of a system for treating a skin condition with phototherapy according to the present disclosure.

Described herein are systems and methods for treating skin conditions. Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As used herein, "skin condition" means any skin condition, disease, or disorder, which may be treated with phototherapy. "Skin condition" includes, without limitation, psoriasis, eczema, and vitiligo.

As used herein, "affected area" means any skin area that is affected by a skin condition. "Affected area" includes, without limitation, skin lesions, areas of scaly skin, areas of discolored skin, rashes, irritations, and skin areas of discomfort, each associated with or caused by a skin condition.

As used herein, "processor" means any computer processor, for example and without limitation, a CPU.

As used herein, "computer-readable storage medium" means any storage medium suitable for reading by a computer, for example and without limitation a RAM.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Treatment of Skin Conditions By Phototherapy

Described herein are systems and methods for treating affected areas associated with skin conditions with phototherapy. Non-limiting examples of affected areas include skin lesions, rashes, irritations, scaliness, discoloration or discomfort caused by one or more or psoriasis, eczema, or vitiligo. Generally, systems described herein for treating skin conditions with phototherapy comprise a phototherapy device, a patient computing device, and a server. Also described here are systems and methods for treating patients with phototherapy for other medical conditions. A non-limiting example of a phototherapy treatment for treating a medical condition other than a skin condition includes vitamin D deficiency.

Skin conditions such as psoriasis, vitiligo, and eczema may be treated by administration of light radiation, such as UV radiation, to the affected area, also referred to as phototherapy. UVB radiation having a wavelength in the range of 300-320 nm is effective in treating certain skin conditions including psoriasis, vitiligo, and eczema. Generally, by applying a dose of UV radiation measured by both radiation intensity and time of exposure, a physician attempts to apply the maximum dosage possible to the area affected by the skin condition without burning the surrounding skin tissue. If the physician observes excessive redness or erythema in the surrounding skin tissue after treatment, she may recommend or prescribe a reduction in the dose. By contrast, if there is no redness or erythema observed, she may recommend or prescribe an increase in the dose.

Traditionally, in order for skin condition patients, for example psoriasis, vitiligo and/or eczema patients, to undergo UV phototherapy, those patients have often been required to attend at a clinician's office, such that the prescribing clinician could be present to administer and/or supervise the treatment, and to observe the effects, for example erythema as discussed above, and adjust the prescribed phototherapy dose accordingly. Additionally, traditional phototherapy treatment protocols require office visits three days per week for many weeks, which is inconvenient for patients, especially patients with traditional work schedules. As a result of these inconveniences, patients suffering from such skin conditions often fail to complete or comply with traditional office based phototherapy regimens.

The advent of home phototherapy has led to the development of equipment that allows the patient to receive phototherapy treatment at a convenient time in the comfort of their home. While these options appear to solve convenience issues, they introduce physician concerns regarding adherence to protocols and follow-up. Physicians are reluctant to prescribe home phototherapy systems that rely on the patient for dose control and schedule without monitoring.

Use of Certain Systems and Methods for Treating Skin Conditions in Patients With Phototherapy Systems and methods described herein address certain of these problems. In use, according to some embodiments, a hand-held phototherapy device as described herein is operable by a skin condition patient at her convenience in her own home or some other suitable place. A prescribing physician may evaluate a patient's skin condition, for example by observing skin affected by psoriasis, vitiligo, or eczema, and prescribe conditional prescription parameters for phototherapy treatment. The prescribed parameters may comprise a standardized, known and established phototherapy regimen, may be customized based on a physician designed, or may be a semi-customized standardized regimen that is adjusted by the physician based on the patient's needs and/or response to treatment. In some embodiments, the system described herein will deliver the same level of control as phototherapy administered within a clinical setting by delivering the prescribed doses in accordance with the protocol and providing records of all treatments.

Referring to FIG. 1 a physician or other qualified health care worker may access a network 101 via a computing device 103 such as a personal computer, mobile phone, or tablet. The physician may input a phototherapy prescription by a suitable user interface. After the phototherapy prescription is communicated to the network it can then be accessed by the patient using a patient computing device 102 such as a personal computer, mobile phone, or tablet. The parameters necessary to carry out the prescription can then be transferred to a phototherapy device 104 by a wired or wireless connection. In certain embodiments, the wireless communication is a Bluetooth™ communication.

As discussed in further detail below, by use of certain systems and methods described herein, the prescribing physician may exercise some control over the home use of the phototherapy device by the patient. In some embodiments, conditional prescription parameters, for example number and location of treatment sites, initial dose, method to determine subsequent doses, method to determine adjustments for missed days, maintenance treatment doses, treatment assessment method, treatment assessment frequency, treatment parameters in case the computing device is unavailable, enablement of the treatment dependent on completion of office visits or consults, enablement of the device dependent on acknowledgment of physician supplied materials, enablement of the device dependent on fulfillment of other physician requests such as user supplied photos, conditions in which the treatment would be disabled, are entered by the physician either directly into a patient computing device to be used or operated by the patient, or into a remote computing device to be used or operated by the physician. This information is then communicated, in some embodiments, from the remote computing device to a server. In turn, this information is then communicated to a patient computing device which, in some embodiments, is to be used or operated by the patient. The patient computing device is configured to transmit a first signal to the phototherapy device, as discussed more fully below, enabling operation of the phototherapy device according to the conditional prescription parameters (e.g. intensity, time, or frequency), activate the phototherapy light source, and transmit a second signal to a server, reporting activation of the phototherapy device.

In some embodiments, the patient inputs information, for example whether and when a treatment has been completed, the degree of redness or erythema observed at the treatment site, size or location of an affected area, disease state, and/or any other observations or notes the patient may have or may be required or requested by the prescribing physician, into the patient computing device. In some embodiments, this patient information is then communicated to the prescribing physician.

Figure 2:
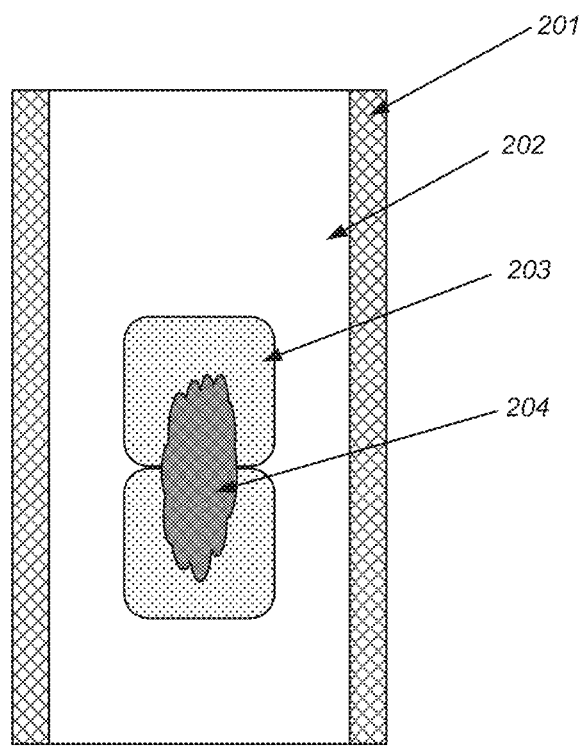
FIG. 2 illustrates a photographic image of treated region and surrounding areas. These treatment regions are separated using image processing techniques so as to determine the color difference between the untreated area and the unaffected skin of the treated area. The phototherapy dose can be adjusted based on this information. For example, the dose could be increased if the unaffected treatment region does not show a color difference from the untreated region. As another example, the dose could be reduced if the red color difference between the unaffected treated region and the untreated region is greater than a predefined threshold. The non-skin background area is shown, as the image processing method will need to identify and remove this area prior to color comparison.
Figure 3A:
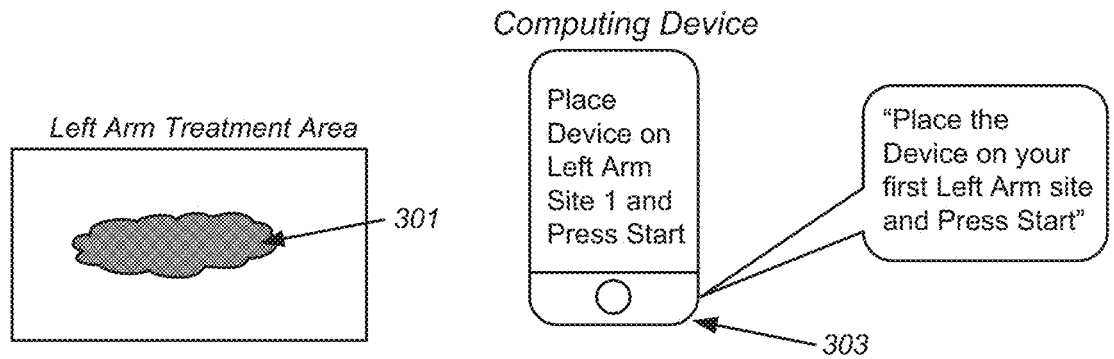
FIG. 3A-G illustrates steps in a method for monitoring skin treatment by phototherapy. A, a patient computing device (e.g., a mobile phone, tablet or laptop) instructs the user where to place the phototherapy device. This can be done by audio or text prompt. B, the computing device tracks the duration of treatment and indicates to the user when the treatment is done. C, optionally, if the site is too large for one treatment, the computing device prompts the user to move to a second area of the affected site. This is repeated until the affected site is completely treated. D, The device tracks the duration of the treatment at the second area. E, optionally, the computing device prompts the user to begin treating an affected site at a different location. F, the computing device tracks the duration of treatment at this location. G, the computing device indicates when all treatments have been completed.
Figure 3B:
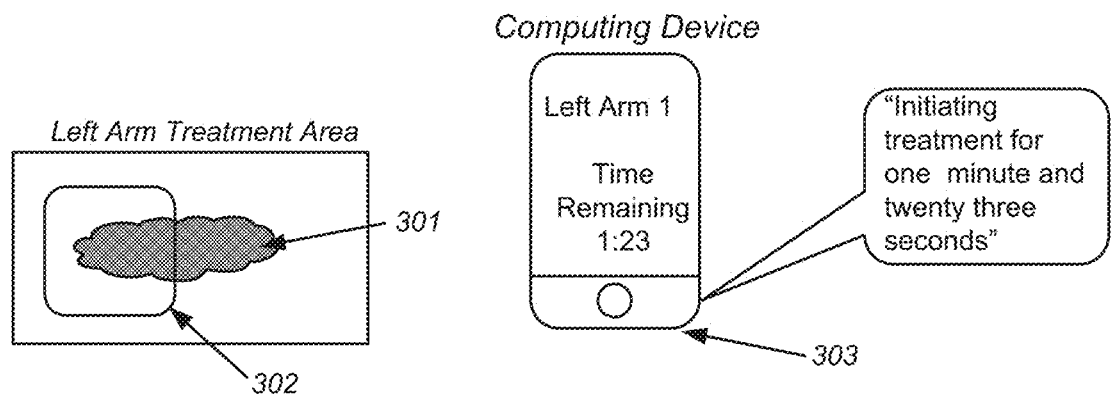
Figure 3C:
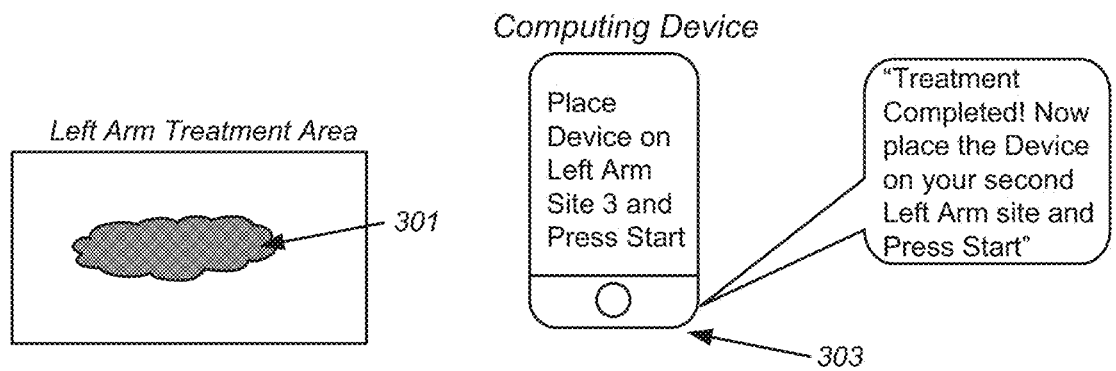
Figure 3D:
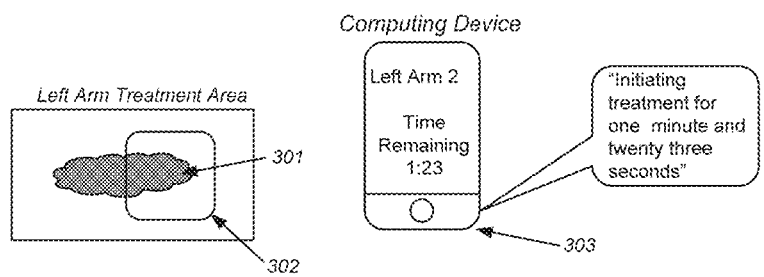
Figure 3E:
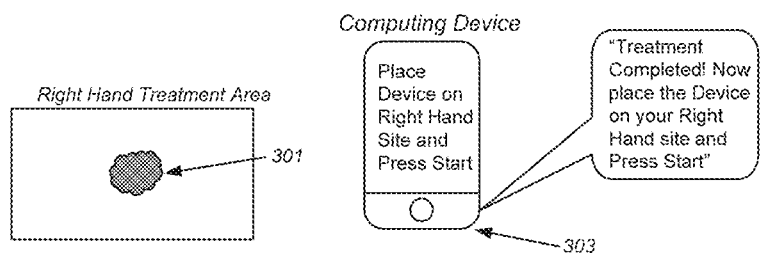
Figure 3F:
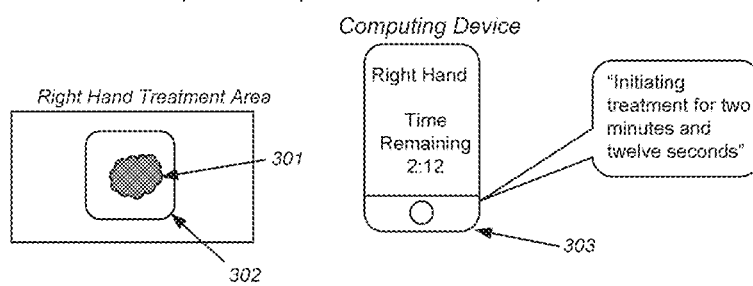
Figure 3G:
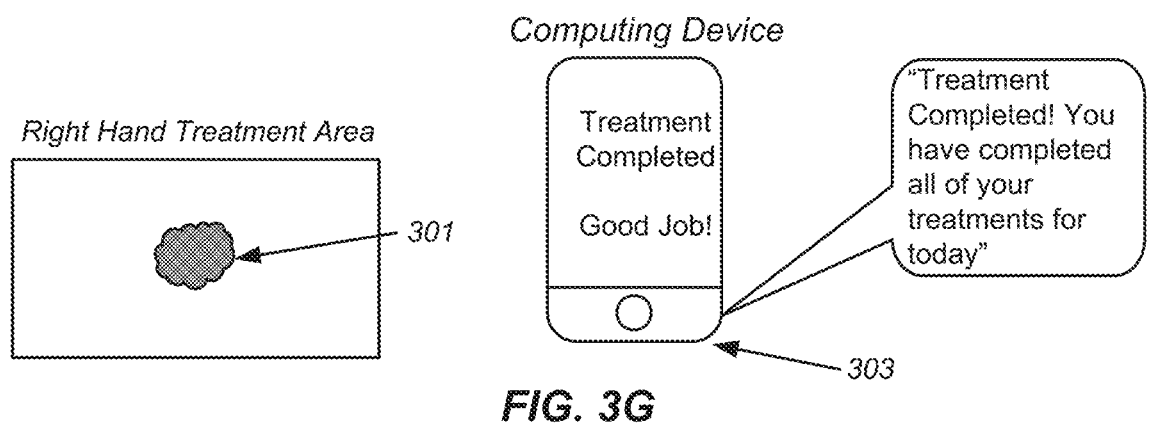

In certain embodiments a patient can photograph an area for treatment and the photograph can be analyzed using image analysis software. This image can be analyzed to develop a treatment plan or adjust the dose for a treatment plan. Referring to FIG. 2 the software can recognize unaffected skin 202 from a non-skin background 201. The software can also recognize an affected area 204 from amongst the healthy unaffected skin 202. The software can also recognize healthy treated skin 203 in cases where there is a color change of unaffected skin due to the treatment. In some embodiments, the healthy treated skin is recognized by identifying colored areas that are similar in shape, or have similar features to the treatment area. In some embodiments the software is able to compare the color of the unaffected treated skin 203 to the unaffected skin 202 and adjust the dose of subsequent treatments based on this color difference. In some embodiments, the software can determine a tiling pattern in order to cover the entire affected area 203 while requiring the fewest treatments or exposing the least healthy skin. Referring to FIGS. 3A-G, a patient with a skin condition 301 is prompted to begin treatment by the patient computing device 303. If the area to be treated is larger than the device's light output area 302, the patient is prompted to continue treatment of the affected site at a different non-overlapping area. This can be repeated until all of the affected site has been treated. The patient can then be prompted to move onto a different area as in FIG. 3C. This is repeated until all treatments have been conducted as shown in FIG. 3G.

In some embodiments, a computing device is configured to direct a user as to how to carry out the phototherapy treatment. In some embodiments, a global positioning system (GPS)-style interface facilitates the user's navigation through the treatment, which may be based on information inputted into either a remote computing system or directly to the patient-operated computing system itself by the prescribing physician. In some embodiments, the patient computing device prompts the user through a series of commands as to how to operate the phototherapy device during the treatment regimen. In some embodiments, the patient computing device prompts the patient, by way of reminders, that it is time to carry out a scheduled treatment regimen.

A GPS-style guidance protocol may be used with multi-dose targeted phototherapy, or with any targeted phototherapy system. Targeted phototherapy involves treating a number of skin areas with a small treatment head and positioning the treatment device only over the specific areas that need to be treated. This treatment process limits unnecessary treatment of unaffected skin and may provide opportunities to increase the local UV doses while maintaining UV tolerance. Administering multiple doses separately may cause difficulty for a user to remember which areas have been treated. In order to facilitate administration of a sequence of treatments, according to certain embodiments of the present disclosure, a method is provided that guides the administrator (e.g., patient or physician) through the process, as a GPS navigation system guides a driver to a destination.

Figure 4:
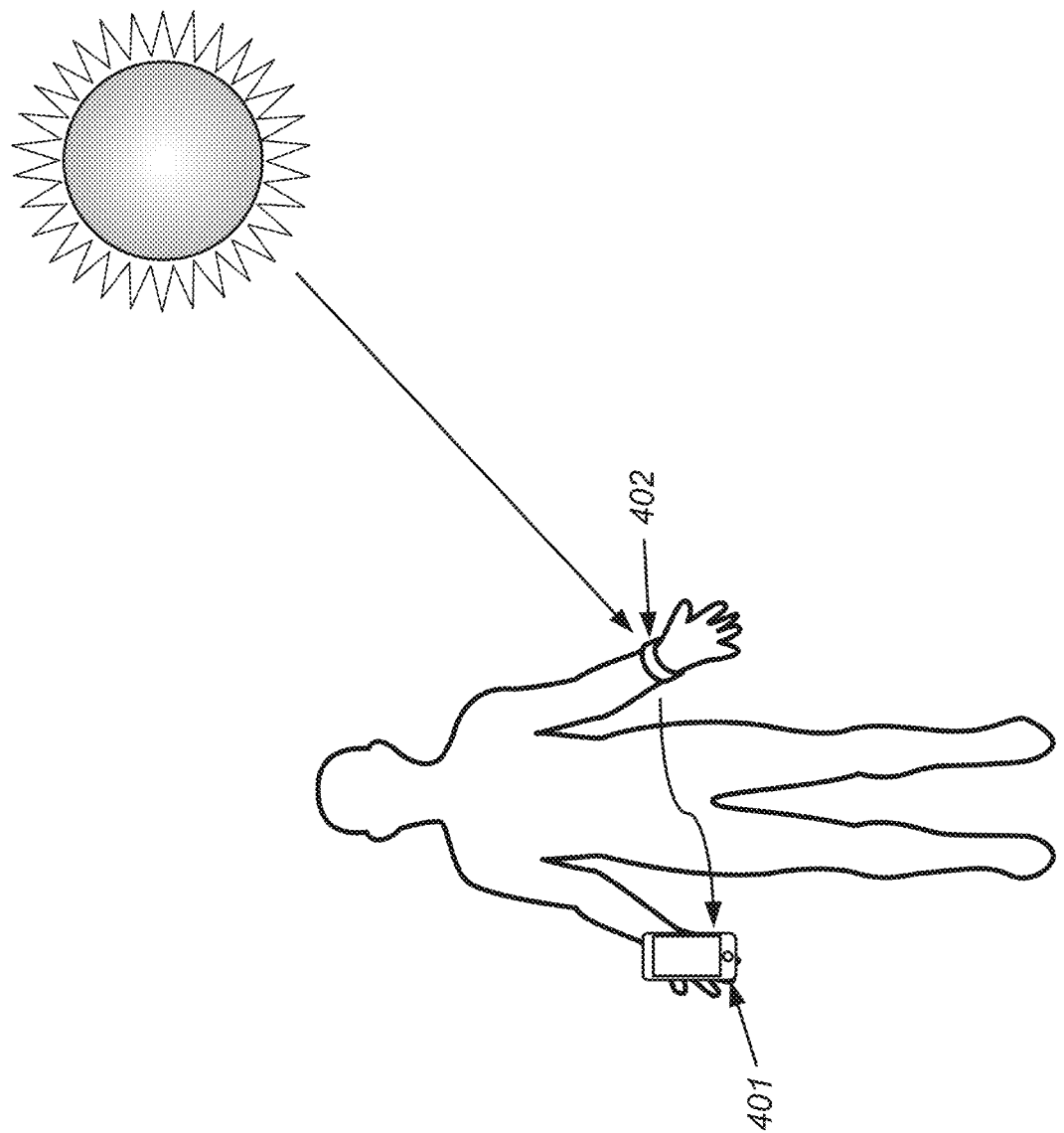
FIG. 4 illustrates one embodiment of the methods and systems of the current disclosure. The patient wears a device comprising a photosensor that measures UV exposure. The UV exposure is communicated to a patient computing device so that a prescribed treatment dose can be decreased accordingly.
Figure 5:
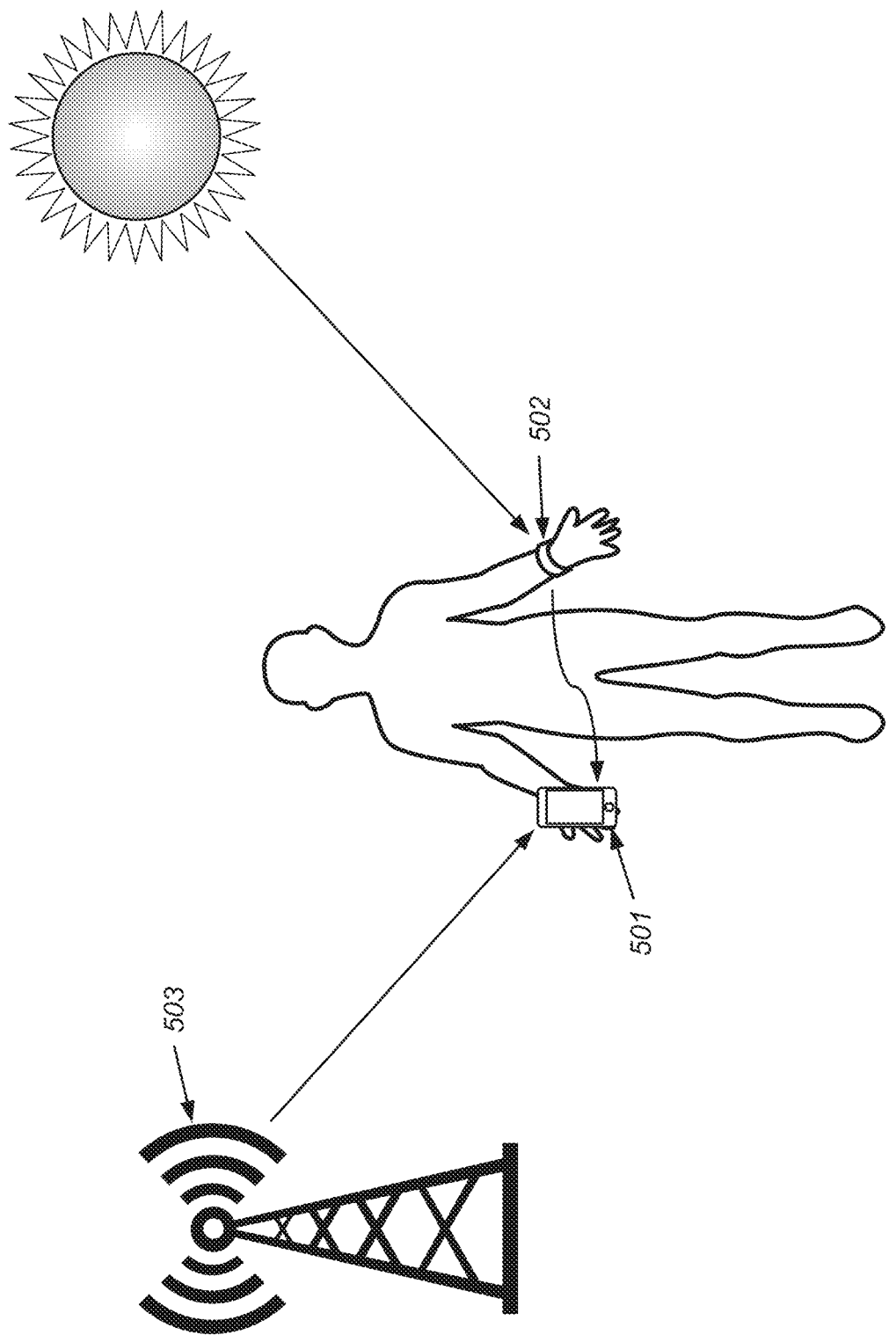
FIG. 5 illustrates one embodiment of the methods and systems of the current disclosure. The patient wears a device comprising a light sensor that senses sunlight. The presence of light is communicated to a patient computing device which also receives UV index information for the time and place of the user. From this information, an estimation of UV exposure can be calculated, so that a prescribed treatment dose can be decreased accordingly.
Figure 6:
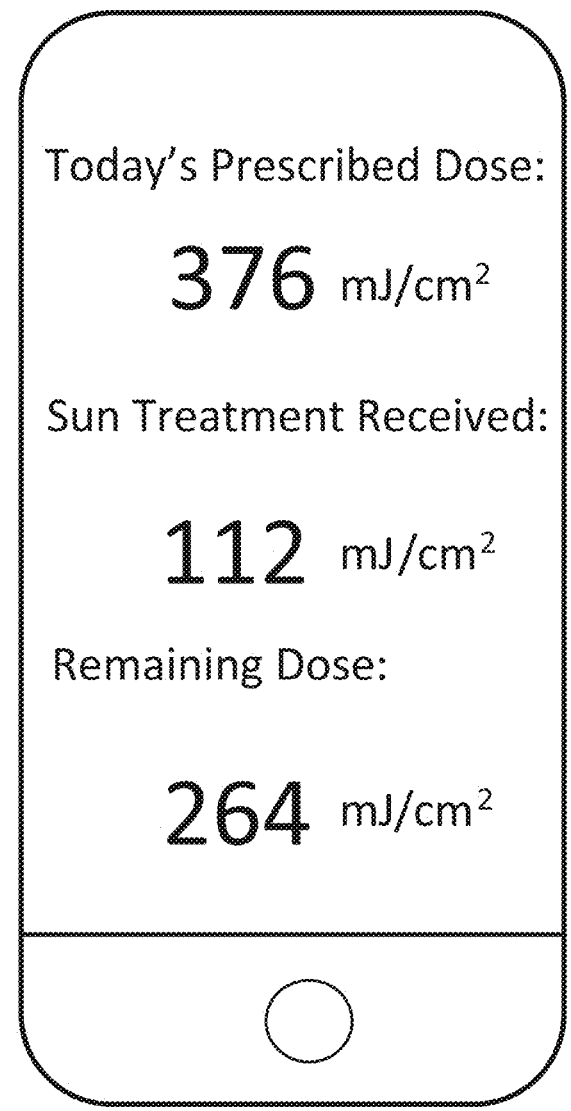
FIG. 6 illustrates a non-limiting embodiment of a graphical user interface that allows a patient to adjust a dose of radiation delivered from a phototherapy device based upon the amount of UV exposure from the sun.

Referring to FIG. 4 a patient may monitor ambient UV exposure by wearing a photo sensor device 402 that communicates to, and stores information about ambient UV light on a mobile device 401. Referring to FIG. 5 a patient may wear a sun detector 502 that communicates to and stores information about sun exposure on a mobile device 501. The mobile device can estimate UV exposure by integrating data about the UV index specific to a certain time and place with the sun exposure information from the sun detector. 503. Referring to FIG. 6 the patient can be informed if a daily treatment needs to modified or reduced based upon ambient sun exposure. This can be communicated through a user interface on the patient's mobile device. Additionally, this information could be communicated to a remote device so that a phototherapy treatment plan could be revised based on UV exposure from the sun.

According to embodiments, methods are provided to estimate or measure therapeutic UV exposure to the sun to fulfill treatment needs or to supplement prescribed phototherapy treatment. The methods involve steps of measuring or estimating UV exposure received by an individual, communicating UV exposure information to a computing device, and comparing the UV exposure to the prescribed treatment. Received UV exposure may be estimated, based on the location and duration of sun exposure, for example by monitoring a patient's location with a GPS device, such as a smartphone, and by using the broadcasted UV index for the nearest location. Received UV exposure may also be determined using a wearable sensor that calculates the duration and time of day of sun exposure. In embodiments, the sun exposure may be determined by manually recording the start time and stop time of sun exposure on a computing device. A patient's location may be determined by a GPS system connected to a computing device, for determining or estimating the patient's UV exposure based on public information about the UV intensity at the time and place of the patient's exposure. In embodiments, the patient's therapeutic UV exposure may be measured by a calibrated photo sensor in proximity to the treatment site during exposure. In embodiments, a prediction may be made as to solar UV exposure required to reach a therapeutic target using at least one of the following: UV index forecast, measured therapeutic radiation, time of day, time of year, location and results from previous sessions. In embodiments, UV exposure levels may be used to provide therapeutic treatment records. In embodiments, a prescribed dose of UV exposure to be received from a UV phototherapy device may be adjusted to account for solar UV exposure received by the patient. In an embodiment, the measured or estimated exposure may be adjusted with a scaling factor to account for differences from angle of incidence, shading, sunscreen, clothing coverage or other factors. In an embodiment, exposure level may be monitored- and and communicated to a user of a phototherapy device, for example a patient or a prescribing physician, using audio and/or visual information in order to ensure that the user does not exceed a target UV dose in view of externally received solar UV exposure.

According to an embodiment, a method is provided to determine the erythema level of unaffected skin within a treatment area. The method includes steps of taking a photographic image of the treatment area and surrounding skin, pre-processing the image to remove non-skin background areas, identifying the treated and untreated regions, by using image processing techniques such as boundary shape identification, computing the red color difference between skin on either side of the boundary, and comparing the red color difference to threshold values to determine whether unaffected skin is normal, pink or red.

According to an embodiment, a method is provided to guide a targeted phototherapy treatment sequence. The method includes steps of communicating, for example by wireless communication means, between a phototherapy device and a computing device, which may be a mobile phone or smartphone device or the like, to synchronize a phototherapy sequence plan to be administered, communicating information to the administrator on the computing device regarding current status of the treatment sequence using audio or visual cues, communicating from the phototherapy device to the computing device when a treatment has been completed, or was interrupted, and communicating the next treatment location to the administrator on the computing device using audio or visual cues. In embodiments, the information communicated to the administrator includes current treatment location and time remaining on treatment.

According to an embodiment, a method is provided to develop evidence-based treatment recommendations from a connected system of phototherapy devices. The method includes steps of collecting outcomes of phototherapy treatments across the system, determining patient criteria of interest such as disease type, severity, age, skin type, years with disease, treatment area locations, geographical location, determining treatment criteria of interest such as dose control method, treatment frequency, missed treatments, maximum dose, correlating patient criteria and treatment criteria to positive outcomes and negative outcomes, and providing evidence based recommendations on treatment plan adjustments for an individual based on correlation evidence.

Components of Certain Systems and Methods Described Herein

Phototherapy devices of the present invention comprise a housing comprising control circuitry as well as a phototherapy light source. In an embodiment, the phototherapy device is hand-held. In an embodiment, the light source comprises one or more light-emitting diodes (LEDs). When activated, the light source emits a light comprising UVB radiation. In an embodiment, the UVB radiation comprises a wavelength in the range of 300-320 nm. It should be understood that radiation in other therapeutic wavelengths may be emitted as well including, for example, radiation in the UVA range. It should also be understood that other light sources besides LEDs are suitable for use with the systems and methods described herein.

In an embodiment, the phototherapy device comprises a processor configured to run software and an application. In an embodiment, the phototherapy device comprises a display screen for displaying a graphic user interface. In an embodiment, the phototherapy device comprises a processor with a timer that adjusts the duration of the treatment in order to control the dose with a fixed power supplied to the light source. In another embodiment, the power supplied to the light source is adjusted, thereby controlling the intensity of the light emitted therefrom.

The phototherapy device comprises a signal receiver for receiving a signal from a signal transmitter in the patient computing device. Any signals described herein are, depending upon the embodiment, wireless, or non-wireless, signals. Any transmitters or receivers described herein are, depending on the embodiment, for transmitting and/or receiving wireless signals, or for transmitting and/or receiving non-wireless signals.

In an embodiment, the phototherapy device is configured to communicate with a computing device. In some embodiments, the computing device is physically incorporated with the phototherapy device, such as by being housed in a common housing. In an embodiment, the computing device is configured to be connected to the phototherapy device by a physical connection, such as a wire or other connection for transmitting signals between the phototherapy device and the computing device. In another embodiment, the computing device is configured to send and/or receive wireless signals to and/or from the phototherapy device. In an embodiment, the wireless signals are transmitted via near-field, Bluetooth™, infrared, radio, or another suitable wireless technology. In an embodiment, the computing device is a mobile telephone device, for example a smartphone. In another embodiment, the computing device is a home computer or laptop computer. In another embodiment, the computing device is a tablet device.

In an embodiment, the computing device comprises a first processor. In a further embodiment, the patient computing device comprises a first display, coupled to the first processor, and a signal transmitter coupled to the first processor. In a still further embodiment, the patient computing device comprises a first non-transitory computer-readable medium encoded with a first computer program including a first set of instructions executable by the first processor. When executed, by the first processor, the first set of instructions causes the first processor to: display a first GUI on the first display; transmit a first signal to the signal receiver on the phototherapy device, thus enabling operation of the phototherapy device; activate the phototherapy light source; and transmit a second signal.

Use of the Described Systems According to Some Embodiments

In use, systems according to some embodiments permit a user to either passively or actively transmit a signal from the patient computing device, for example a smartphone, to the phototherapy device. In some embodiments, the signal enables operation of the phototherapy device, for example allowing activation of the phototherapy light source. In some embodiments, the parameters of this operation, for example the duration and/or intensity of the phototherapy treatment, may be determined by the signal transmitted by the patient computing device to the phototherapy device.

In an embodiment, the system further comprises a server, which is configured to communicate with the patient computing device, and to receive a second signal therefrom. In an embodiment, the server comprises a database of patient records and prescribed treatment protocols, comprising prescription parameters. In an embodiment, the server stores patient information and/or patient records about a patient receiving or scheduled to receive phototherapy treatment. In an embodiment, the patient records comprise one or more of the following: treatment dates and times, treatment durations, applied treatment energies, treatment site photos, analysis of treatments site photos, patient/physician correspondence, assessments of treatment sites, and changes to the treatment protocol.

In an embodiment, the server is configured to perform analysis of patient records, prescribed treatment protocols, and outcomes over populations of patients. In an embodiment, the server is configured to perform computational analysis. In an embodiment, the computation analysis is an analysis of degree of erythema of a treated area of skin and surrounding skin tissue. In another embodiment, the computational analysis comprises an analysis of treatment progression comprising size and severity of disease.

In use, according to some embodiments, a user inputs patient information into the patient computing device, for example by use of a smartphone app. The patient information may be manually inputted by the patient, for example by selecting options from menus, by typing in notes, or by taking a photograph of a treated area and uploading that photograph into the patient computing device. In an embodiment, the patient computing device is configured to present an interface that allows the patient to capture an image of a treated area of skin and surrounding skin tissue. In an embodiment, the patient computing device comprises a camera for capturing such an image.

In an embodiment, the remote computing device is configured to present an interface that provides guidance to the patient for operation of the phototherapy device. In certain embodiments, the remote computing device is configured to present an interface providing a treatment schedule, treatment reminders, and/or directions for how to use the phototherapy device.

In an embodiment, the phototherapy system includes a second computing device that is a remote computing device. The remote computing device is configured to communicate with the server, and comprises a processor and a memory. The remote computing device is configured to present a graphic user interface, allowing a physician or other health care provider to set one or more conditional prescription parameters, review information pertaining to operation of the phototherapy device, and adjust the conditional prescription parameters, to transmit a first communication to the server, and to receive a second communication from the server. In an embodiment, the first communication is transmitted from the server to the patient computing device.

In an embodiment, the server is configured to determine an initial phototherapy dose for treatment, based on the user's skin type, or susceptibility to erythema of the user or patient. For instance, where patients are known to have a skin type that is generally associated with susceptibility to erythema, or if it is known that an individual patient is susceptible to erythema when exposed to UVB radiation, the initial phototherapy dose determined is lower than where patients are known to be relatively unsusceptible to erythema.

In use, in an embodiment, the remote computing device is operated by a prescribing physician or an assistant of the prescribing physician, or some other health care professional. In some embodiments, the prescribing physician uses the remote computing device to review patient information displayed in a GUI. In some embodiments, the prescribing physician runs an application on the remote computing device to facilitate interaction with the patient information, and/or to monitor treatment progression, and/or to adjust the treatment parameters.

Computing Device

In some embodiments, the system and method described herein include a computing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

Non-Transitory Computer Readable Storage Medium

In some embodiments, the system and method disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

The World Healthcare Organization estimates that adherence to prescriptions for chronic diseases, including chronic skin diseases such as psoriasis and vitiligo, in developed countries averages around 50%. There are many factors that contribute to this low adherence rate, and improvements to adherence may result in better outcomes and lower cost of treatment.

Phototherapy treatment regimens have traditionally suffered from low adherence rates which are thought to be attributable to several possible factors. Phototherapy clinics are often inconvenient for patients, often requiring clinic visits three times per week during normal business hours. Motivation to maintain a demanding schedule that can interfere with work is highest among the most severe cases of psoriasis, however the vast majority of patients have been diagnosed with mild cases. The present disclosure provides home phototherapy systems and methods that may allow patients to self-administer treatment according to their individual schedules while allowing the patient or her physician to manage the phototherapy schedule and dosing regimen.

Studies have shown that adherence improves when patients are reminded about their schedule and also if they know that someone else is counting on them. In one home phototherapy study, Yarbrough et al., *Journal of American Academy of Dermatology*, vol. 60, no. 5, which is incorporated herein in its entirety by reference, adherence was charted at 100% during the 12 week clinical study. At the end of the 12 week study, the subjects were allowed to retain the equipment and continue treating themselves. During that time the phototherapy device use was monitored and adherence immediately dropped to 60%.

Phototherapy systems and methods provided according to embodiments of the present disclosure may provide improved adherence in the following manner.

A physician may prescribe a minimum adherence level to a patient, and the patient will know that their adherence level is being monitored. A remote computing device is configured to allow a minimum adherence level to be prescribed. The prescribed minimum adherence level may be communicated to the patient, for example by communicating the minimum adherence level to the patient computing device. The phototherapy device may then be electronically monitored for use to determine the adherence level, available for patient and physician to view, for example via a remote computing device (physician) and a remote computing device (patient). The physician may then be notified if the adherence level drops below the minimum level.

The phototherapy device may be configured to communicate with the patient's remote computing device (e.g. a mobile smartphone), which is configured to execute an application that maintains the phototherapy schedule and provides reminders to the patient on treatment days to improve likelihood of maintenance of the treatment schedule. This maintenance/reminder system may be configurable to allow patients to find convenient time windows for treatment.

In some embodiments, the application communicates positive reinforcements to the patient, including messages of encouragement, badges of achievement and incentives to complete treatment (e.g. financial payment, coupons, charitable donations . . . ).

In some embodiments, the application electronically connects the patient to support groups such as family, friends, advocacy groups, social media groups, healthcare providers and the manufacturer. Connected support group members may be automatically notified under certain conditions or upon the occurrence of certain event (e.g. when a treatment is missed, upon each successful treatment, when adherence drops below a minimum). The patient may also be able to communicate with the support group regarding their therapy.

In some embodiments, the application may be configured to communicate the value of treatment to patients to explain or underscore treatment importance to the patients. Such configuration may be of particular importance for treatments that take a long time to result in any visual result or effect, and/or in cases where patients do not present any visual sign of any disease or condition.

In some embodiments, the application may be configured to question patients as to why a treatment has been missed, and collected information may be employed by the application, the patient, and/or the prescribing physician in order to proactively resolve unforeseen adherence or compliance issues with future treatments.

Conventional non-targeted phototherapy methods involve irradiating the entire body with UV light, either with a booth that surrounds the subject, or with light panels where the subject stands facing the panel. For such treatments the entire body may be irradiated with the same dose. The dose level of all treatment locations is therefore limited by the tolerance of the most sensitive area of the body. In cases where the entire body does not need to be irradiated, areas that do not require treatment may, according to such conventional methods, be masked with an article of clothing.

By contrast with such entire-body methods, targeted phototherapy involves a small treatment head that confines the treatment to a local area. The treatment head is then moved around from site to site to treat the areas that need treatment, while minimizing unnecessary irradiation to unaffected skin. Additionally, targeted phototherapy often allows administration of higher doses, which can lead to faster results. Targeted phototherapy requires the administrator to keep track of which areas have been treated. If the treatment areas are overlapped, then the overlapping areas will receive double the dose which will likely result in a burn. If there are gaps within the treatment areas, then these will not benefit from the treatment.

According to systems of the present disclosure, individual sites may be treated with different doses. According to some embodiments, areas of the body with a darker skin color may be treated with higher doses of UV than areas of the skin with lighter color, since it is believed that darker skin may have increased tolerance to UV light and require a higher dose of UV exposure in order to provide the same therapeutic effect or degree of erythema. According to some embodiments, thicker-skinned areas of the body are treated with higher doses than thinner-skinned areas of the body, since it is believed that thicker skin may reduce penetration and therefore require a higher dose of UV exposure in order to provide the same therapeutic effect or degree of erythema.

In some embodiments of the present disclosure, methods are provided whereby dosing generally increases over time with the treatment protocol. In some embodiments, treatment of an area of skin presenting a recently formed skin condition may be treated with a lower dose of UV exposure, as compared with an area of skin presenting a skin condition which is further advanced up the treatment dosing curve. In some embodiments, the physician and/or the phototherapy patient may be guided through a targeted phototherapy process, to reduce the likelihood of a mix-up or user error resulting in the wrong UV dosage being applied to one or more of the treatment areas.

According to some embodiments of the present disclosure, phototherapy systems are configured to maintain and track doses on individual treatment sites independently by utilizing a computing device and the following method. Treatment sites are independently identified, and the physician, patient, or other treatment administrator is guided through a sequence to such that the phototherapy device is placed on the proper treatment location as each dose is queued. This guidance can include visual and audio cues provided to the treatment administrator. Subsequently, independent treatment sites are treated following the same protocol to determines how the dose changes over time. After treatment of a number of sites, one or more individual sites are independently assessed to determine whether each site dose is to be increased, maintained or reduced (this determination may be based, for example, on the post-treatment color or degree of erythema of skin surrounding the area affected by the skin condition). Sites that are more sensitive (e.g., those of lighter or thinner skin) may correspond with slower increase in dose as compared with less sensitive sites (e.g., those of darker or thicker skin) a composition is applied to the skin surfaces prior to treatment that will change color once treated, to reduce the likelihood of a mix-up or user error resulting in the wrong UV dosage being applied to one or more of the treatment areas.

In some embodiments, the phototherapy system computes planned subsequent doses for individual sites and stores that information. The system then retrieves the planned doses for each site at treatment time and communicates those doses to the phototherapy device. Newly added sites start at the beginning of the protocol with a prescribed initial dose.

Phototherapy involves providing a controlled dose of light, for example artificial light with known spectral characteristics, whereas heliotherapy involves using sun exposure to treat the body. It is possible to treat skin diseases such as psoriasis, eczema and vitiligo with the sun, however, aspects of such treatment may be difficult to manage, since only a small fraction of light emitted from the sun is therapeutic (approximately 0.3%) and the spectral output and power vary widely based on the weather, time of day, altitude and other environmental conditions. The World Health Organization has adopted a standard for UV exposure (the UV Index) that is based on typical erythema response of skin. The action curve for treatment of skin diseases corresponds with the erythema curve in the therapeutic range of 300-320 nm, and the UV Index may be used to provide a reasonable estimation of the therapeutic power of the sun. The UV Index is a measured or calculated value that is widely available on an hourly basis from most major cities. Based on the date and times of sun exposure, one may estimate the degree of UV exposure, and thus estimate the extent of therapeutic exposure received during that sun exposure.

For patients using phototherapy, it may be advantageous to compensate for exposure from the sun within their phototherapy treatment plan, and to adjust their treatment plan based on sun exposure received. Known phototherapy protocols are based upon the assumption that patients are not receiving any appreciable UV exposure other than the exposure provided by the phototherapy equipment. Known protocols and methods involve instructing patients to avoid sun exposure and to use sunscreen if they are being treated with phototherapy, since patients that are exposed to UV from the sun may be at risk of burning if their phototherapy treatment plan does not compensate for sun exposure.

For skin disorder patients using heliotherapy only, known tools do not accurately quantify and monitor the doses delivered, leading to sub-optimal therapy. For example, a wide range of UV Index values exists, depending on location, season, time of day and other weather anomalies. A UV Index range of 0.5 to 10 may exist at the same location depending on season and time of day, meaning that exposure could vary by a factor of 20. To achieve the same degree of UV exposure of a UV index of 10 over 10 minutes, would require a 200 minute (3 hours, 20 minute) exposure with a UV Index of 0.5.

Known protocols for phototherapy adjust the UV dose based on observations from a previous treatment. A target dose for phototherapy is the maximum UV dose that will not cause erythema (burning) of the unaffected tissue surrounding an area affected by a skin condition. When assessing the surrounding unaffected tissue, the dose adjustment may be increased if no skin color change is evident, maintained if a slight pink color is evident, and reduced if the surrounding skin appears red.

For home phototherapy systems according to the present disclosure, an objective measure of the erythema level is obtained using an image taken with a digital camera. Computing color on digital camera images depends on lighting and camera position. According to systems provided according to some embodiments of the present disclosure, methods are provided to account for these differences by including calibrated color cards in the image. According to some embodiments, methods are provided employing calibrated colorimeters to account for the differences. According to some embodiments, a method is provided that employs an algorithm for objectively determining the color of surrounding unaffected skin during a phototherapy treatment. According to some embodiments, the algorithm uses a single image, for example taken from a mobile phone camera, and uses a differential measurement technique to subtract out lighting and other camera differences.

Known phototherapy protocols are based on manually collected data available to the using known equipment and processes. Given the limited availability of data, differences in equipment and patient population differences, improvements may be made to a phototherapy treatment plan for an individual patient based on knowledge of outcomes from statistically significant population data. According to embodiments of the present disclosure, a system is provided that creates a large phototherapy records database, including controlled records, for providing recommendations based on analysis of mass data and associated outcomes. According to some embodiments, evidence-based recommendations may be provided to clinicians for individuals that they are treating.

Targeted phototherapy can minimize treatment or UV exposure of unaffected skin by using a small confined treatment area that may be strategically placed on targeted areas of skin that require phototherapy treatment. For treating skin areas that are larger than the device treatment area, the device may be successively moved to adjacent locations in order to treat the entire skin area. This "tiling" process is complicated by the need to identify areas that have been treated to avoid either double treating an area or missing an area that requires treatment.

Figure 7A:
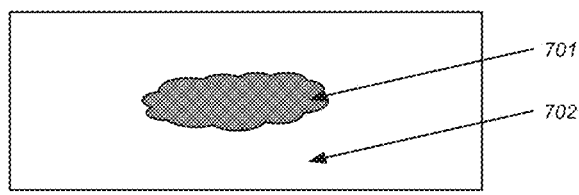
FIG. 7A-E illustrates steps in a method for monitoring skin treatment by phototherapy. A, depicts a patch of skin containing an affected area. B, depicts application of a composition comprising an indicator that fades upon exposure to UV light over and around the affected area. C, depicts that as the composition is exposed to UV the indicator fades signifying that treatment for that area is complete. D, depicts that after treatment of a first area is complete the affected skin is exposed at a second area. E, depicts that exposure to ambient UV will cause any excess indicator to fade.
Figure 7B:
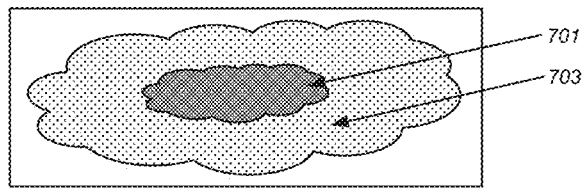
Figure 7C:
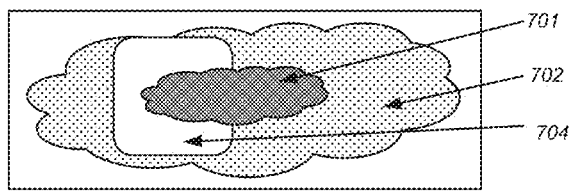
Figure 7D:
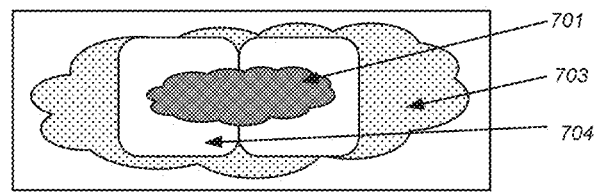
Figure 7E:
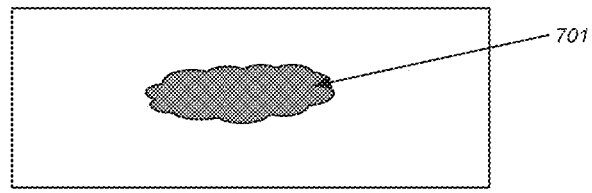

Referring to FIG. 7A-E a patient with an affected skin area 701 amongst healthy skin 702, can apply a composition 703 as shown in FIG. 7B. The composition may contain an indicator dye that changes color, appears or fades upon exposure to UV light. After a treatment has been carried out the composition indicates the treated area 704 as shown in FIG. 7C. This allows for much more accurate tiling of the treatment and minimizes unnecessary UV exposure.

Known phototherapy methods require inking of the treatment area such that a phototherapy administrator may identify placement areas of the device. This solution does not provide knowledge about which of the inked areas have been treated and is inconvenient as it requires a careful inking process and washing to remove the ink. According to embodiments of the present disclosure, a process is provided for identification of areas that have been previously treated. According to an embodiment, a treatment area is covered with UV sensitive dye or photo dye that visibly shows the exposed area. The dye may be UV transparent, or UV transparent after it quickly changes color. The dye may be included in a mixture also comprising an emollient. In embodiments, the emollient may be adapted to enhance the optical uptake of UV energy into the skin. According to an embodiment, the emollient has an index of refraction close to that of healthy skin, for example approximately 1.55. According to an embodiment, the emollient is UV transparent and has a resulting high efficacy when used in conjunction with UV phototherapy. According to embodiments, an emollient is provided including a photo-dye, functioning to display treated areas during the phototherapy process.

According to an embodiment, a UV fade dose for the dye would be larger than an ambient indoor UV dosage received within a short time, such as 15, 20, 30, or 30-60 minutes, and/or smaller than that received under ambient or low sun conditions during a short time, such as 5, 10, 15, 20, or 30 minutes of outdoor daytime exposure to such sunlight conditions such that the dye would not fade under indoor conditions absent administration of phototherapy with a phototherapy device and the dye would fade under outdoor conditions. According to an embodiment, the fade dose is smaller than a dose of radiation received during a first time period, for example a first 2, 3, 4, 5, 10, or 30 seconds of exposure to UV radiation from a phototherapy device. According to embodiments, a dye's fade dose varies with its wavelength sensitivity. According to embodiments, the dye has a higher sensitivity to UVB radiation than to other forms of UV radiation, allowing a user to distinguish between UVB radiation exposure from a phototherapy device and sunlight UV exposure.

According to an embodiment, a composition is provided for application to a region of a patient's skin including an area of a skin affected by a skin condition, in association with application of UV light to the affected area of skin for UV phototherapeutic treatment of the skin condition, the composition comprising an emollient base, for example mineral oil, which may have an index of refraction of approximately 1.55, for facilitating the absorbance of the applied UV light into the affected area of skin and a UV-fading dye. The UV-fading dye, is present in the composition in an concentration suitable for temporarily staining the patient's skin upon application of the composition to the patient's skin, and for fading upon exposure to the applied UV light, thereby indicating where the UV light has been applied to the patient's skin. In embodiments, the dye is present in a concentration suitable for fading upon exposure to ambient sunlight conditions.

In an embodiment, a composition comprising UV-fading dye is administered to a patient's skin affected by a skin condition, UV light is applied to the patient's skin affected by a skin condition in an amount suitable for providing a phototherapeutic effect to the affected skin, and an observation is made as to where on the region of the patient's skin the UV-fading dye has faded, thereby determining where the UV light has been administered to the patient's skin.

Phototherapy Devices

Figure 8:
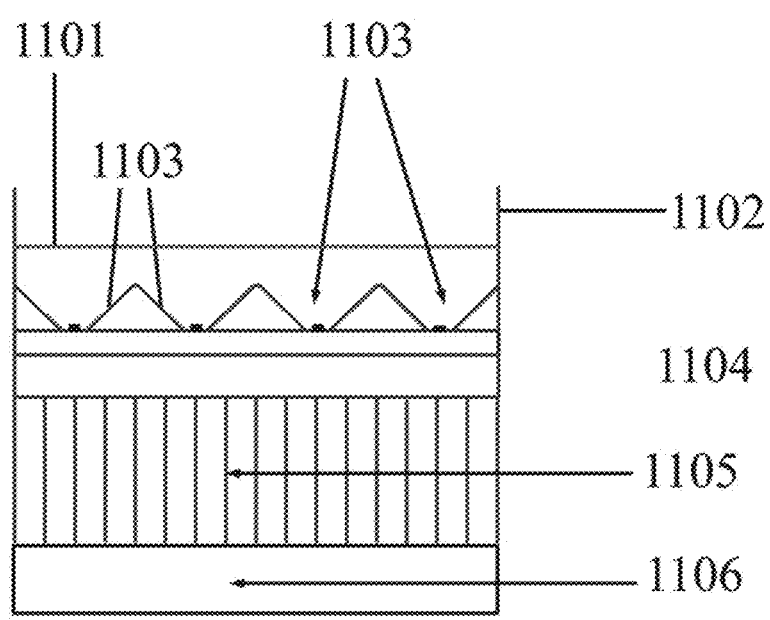
FIG. 8 illustrates a side view of a non-limiting embodiment of a phototherapy device for use with the systems and methods described herein.

Many different phototherapy devices can be used with the systems and methods of the disclosure. One such device is shown in FIG. 8. The device is handheld and comprises an optical filter 1101, a shroud or light guide 1102, reflectors 1103, LED bulbs capable of producing a UV wavelength 1104, a heatsink 1105, and a cooling fan 1106.

Computer Program

In some embodiments, the system and method disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, TCL, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the system and method disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the system and method disclosed herein include one or more databases, or use of the same. In view of the disclosure provided herein, those of skill in the art will recognize that many databases are suitable for storage and retrieval of patient information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

EXAMPLES

The following illustrative examples are representative of embodiments of the software applications, systems, and methods described herein and are not meant to be limiting in any way.

Example 1

Jane is diagnosed with a mild case of psoriasis on her elbows and right leg. Her doctor discusses the treatment options with her and together they determine that targeted home phototherapy is the right treatment for her. After meeting with her physician, she is provided with a box containing a hand-held phototherapy device, and instructed that her prescription will be filled at the office and automatically populated into the device via her mobile phone. She is also instructed to download the Skylit Phototherapy App on her mobile phone, in order to interface with the device and the physician.

The physician launches the Skylit Phototherapy Portal, a web based software application, on her office computer. She enters Jane's patient information, including her skin type, lesion sizes and locations, and selects a treatment protocol from a list of options. The protocol indicates the initial dose that the physician is prescribing and the dose adjustment method. The physician also attaches patient information that will be downloaded to Jane. Since this is Jane's first experience with phototherapy, the physician submits a few post-treatment questions for Jane to answer and requests photos of the treatment sites. The physician also requests an office visit after the first two weeks of treatment.

Jane returns home and opens the box. The phototherapy device consists of a small handheld device with a charging cable. Also included in the box is a set of UV protection goggles. She plugs the device into the charging cable and proceeds to download the Skylit Phototherapy App onto her mobile phone. Jane runs the Skylit Phototherapy App and she notes that her treatment regimen is already loaded. She reads the patient information that the physician provides, and acknowledges having received the information. The Phototherapy App shows the schedule including treatment days, assessment days, office visits and information requests. Jane reviews the schedule and notes that her first therapy sequence is scheduled for the next day.

The next morning, Jane's phone displays a reminder that her therapy is due to be completed that day. She decides to proceed with the therapy and requests initiation of the therapy from within the Phototherapy App. The App indicates that she will be receiving a sequence of 4 treatments consisting of right elbow, left elbow and two adjacent treatments on the right leg. She is informed about the dose and approximate time that each treatment in the sequence will last. The phototherapy sequence is sent to the device, and she listens to an audio confirmation that her device is enabled. Her phone enters into navigation mode and provides audio and visual indications guiding the treatment sequence in a manner similar to a GPS navigation system.

Jane picks up the handheld phototherapy device and notes that the display also indicates the site, time, and dose of the first treatment. She puts on her UV protection goggles, places the device on her right elbow and presses the start button. The device glows a cool blue color as the treatment is administered. At the conclusion of the first treatment she hears an audible sequence of tones from the device and the navigation system on her phone indicates that the first treatment is completed successfully.

The phototherapy navigation system on the phone directs Jane to apply the device to her left elbow and to actuate the second treatment. Jane places the device on her left elbow, presses the start button, and completes the second therapy. The phototherapy navigation system on the phone indicates that the next two therapies are adjacent therapies that will take two treatments to cover the area. Jane is directed to apply the device to the first area and press the start button. After completion of the first area, the navigation system directs her to apply the therapy to the adjacent site and to press the start button. After completion of the therapy sequence, the device indicates that the therapy sequence has been successfully completed. Jane removes the device from the treatment area and powers the device down. She plugs the device into the charging cable and returns to her phone.

The Skylit Phototherapy App indicates that the treatment sequence is successfully completed and prompts her to answer a few questions from her physician about her first treatment. Jane answers the questions and adds a note to the physician that the treatment was simple and went well. The Skylit Phototherapy App shows the updated schedule of phototherapy events and indicates that the next scheduled activity is a color assessment planned for the next day. On the following day, Jane's phone reminds her that she needs to complete a color assessment of her treatments. At her convenience, she launches the Skylit Phototherapy App and is asked to assess the redness color (no redness, pink, red) of each treatment site. She is informed that this assessment is to be used to make an adjustment in her treatment. Jane completes the assessment and the Phototherapy App indicates that her physician requests a photo of the treatment sites. Using the camera included in her mobile phone, Jane takes a photo of each treatment site and the photos are automatically uploaded to her patient file.

On the next treatment day, Jane receives a reminder from her phone that her next treatment is ready. At her convenience, Jane launches the Skylit Phototherapy App and proceeds. The Phototherapy App indicates that her treatment dose has been increased for her right elbow and left elbow, since there is no sign of redness, but the treatment dose will remain the same for her right leg. She is informed that her treatment sequence is enabled and the approximate duration of each treatment. Jane unplugs the phototherapy device from the charging cable and puts on her UV goggles. The display indicates the information for the first therapy and her phone enters navigation mode to guide her through the sequence. She completes the treatment sequence in the same manner as previously. Jane's physician decides to check up on her and gain access to her patient file using the Skylit Phototherapy Portal on her office computer. She notes that Jane has successfully completed two treatments and indicates that everything is going well. She leaves a note for Jane to continue with the treatments and contact her if there are any issues.

Example 2

Mary has been recently diagnosed with a mild case of psoriasis on her scalp. Her doctor discusses the treatment options with her and together they determine that targeted home phototherapy is an appropriate treatment for her. Mary does not own a smartphone, but is comfortable using her computer to download therapy sequences, so she and her doctor agree that this will be the best method for her to use to control the administration of her treatments.

After meeting with her physician, she is provided with a box containing a hand held phototherapy device and is instructed that her prescription will be filled at the office and available for downloading by her computer. Her physician launches the Skylit Phototherapy Portal, a web based software application, on her office computer. She enters Mary's information, including her skin type, and selects a protocol from a list of options. The protocol indicates the initial dose that the physician is prescribing and the dose adjustment method. The physician also attaches patient information that will be downloaded to Mary. Since this will be Mary's first experience with phototherapy, the physician submits a few post-treatment questions for Mary to answer. The physician also requests an office visit after the first two weeks of treatment.

Mary returns home and opens the box. The phototherapy device consists of a small handheld device with a USB cable. Also included in the box is a set of UV protection goggles. She plugs the device into her computer using the USB cable. Mary runs the Skylit Phototherapy App from her web browser and she notes that her treatment regimen has already been loaded into the system. She reads the patient information that the physician has provided and acknowledges that she has received the information. The Phototherapy App shows the schedule, including treatment days, assessment days, office visits and information requests. Mary reviews the schedule and notes that her first therapy sequence is scheduled for tomorrow.

The next morning, Mary receives an e-mail reminding her that her therapy is ready. She proceeds with the therapy. She launches the Phototherapy App from her browser and notes that the App indicates she will be receiving a sequence of six treatments for her scalp. She is informed about the dose and approximate time that each treatment in the sequence will last. She is also informed that there will be multiple adjacent treatments on the scalp, so she will be placing the device in adjacent areas and rotating the device several times prior to treatment to displace the hair in the scalp area. The phototherapy sequence is sent to the device and she hears an audio confirmation that her device is enabled.

Mary disconnects the phototherapy device from the USB cable and brings the device into the TV room to complete her therapy. She notes that the display indicates the site, time and dose of her first treatment. She attaches the scalp accessory over the optical end of the device and puts on her UV protection goggles. Mary places the device on the leftmost area, rotates the device a few times to minimize hair blocking the treatment and then presses the start button. At the conclusion of the first treatment she hears an audible sequence of tones from the device.

Mary removes the device from the treatment area and views the display. The display indicates the first therapy has completed successfully and the second is ready. Mary places the device adjacent the first treatment area and rotates the device a few times. She presses the start button to initiate the second treatment. Mary repeats the process to complete all of the treatments in the sequence. The device indicates that the treatment sequence is successfully completed.

Mary removes the device from the treatment area and powers the device down. She returns to the computer, plugs the device back in to the USB port and returns her focus to the computer screen. When she plugs the device into the computer, the Skylit Phototherapy App uploads the treatment records and indicates that the treatment sequence has successfully completed. She is also prompted to answer a few questions from her physician about her first treatment. Mary answers the questions and decides to add a note to the physician that the treatment has gone well. The Skylit Phototherapy App shows the updated schedule of phototherapy events and indicates that the next scheduled activity is a color assessment planned for the next day.

On the following day, Mary receives an e-mail reminder that she needs to complete a color assessment of her treatments. At her convenience, she launches the Skylit Phototherapy App and is asked to assess the redness color (no redness, pink, red) of her scalp. She is informed that this assessment will be used to make an adjustment in her treatment. Mary uses a hand mirror and the bathroom mirrors to view the treatment area and complete the assessment.

On the next treatment day, Mary receives an e-mail reminder that her treatment is ready. At her convenience, she launches the Skylit Phototherapy App. The Phototherapy App indicates that her treatment dose has been increased since there is no sign of redness. She is informed that her treatment sequence is enabled, and the approximate duration of each treatment. Mary removes the device from the USB cable and moves to the TV room to complete her therapy. After completing the treatment sequence, Mary plugs the device back into the computer. The Phototherapy App indicates that the treatment has been successful. Mary's physician decides to check up on her, and gains access to her patient records using the Skylit Phototherapy Portal on her office computer. She notes that Mary has successfully completed two treatment sequences and indicates that everything is going well. She leaves a note for Mary to continue with the treatments and to contact her if there are any issues.

Example 3

Dale has been recently diagnosed with a mild case of eczema on the back of both legs and on both thighs. His doctor discusses the treatment options with him and together they determine that targeted home phototherapy is an appropriate treatment for him. Dale is not comfortable utilizing technology to drive his treatments, so his physician decides to prescribe a fixed treatment sequence to be programmed into the device at the physician's office.

The physician launches the Skylit Phototherapy Portal, a web based software application on his office computer. He enters Dale's information and selects a protocol from among the options. The physician modifies the protocol settings by selecting an option to prescribe a treatment sequence download. This option disables the dose adjustment feature. He enters a prescription for six treatment sequences to be delivered on each Monday, Wednesday and Friday over the following two weeks. He also selects an option to have the device programmed in the office.

The physician provides Dale with patient information and schedules a follow up appointment after the first two weeks. He informs Dale that a clinician will program the device and show him how to use it. The clinician enters the room with a box containing his phototherapy device. He opens the box and removes the device. The clinician shows Dale how to use the device and answers Dale's questions. The clinician launches the Skylit Phototherapy App on his tablet and downloads the therapy sequences to the device.

Dale returns home with the device and plugs the device into a wall plug USB charger. The next morning, Dale picks up the device and powers it on. The device indicates that the therapy sequence is ready for him. He decides to continue with the treatment sequence. After reminding him to wear safety goggles, the device indicates that he has a sequence of eight treatments. After acknowledging, he notes that the display indicates the site, time and dose of the first treatment. He puts on his UV protection goggles, places the device on the first treatment site and presses the start button.

The device glows a cool blue color as the treatment is administered. At the conclusion of the first treatment he hears an audible sequence of tones and notices that the blue light has turned off. The device display then indicates the site, time, and dose of the second treatment. He places the device over the second treatment site and completes the second therapy. Dale repeats the process for all eight treatment sites. After completion of the therapy sequence, Dale removes the device from the treatment area. He notices that the device display indicates that the therapy sequence has been successfully completed.

Dale powers the device down and plugs the device into the USB cable to charge in a wall plug. The next day, Dale returns to the device and powers it on. The device indicates that treatment is scheduled for the next day. Dale returns the following day and proceeds through the treatment sequence without any problems. He completes the treatment sequence on the scheduled days for the following two weeks in accordance with the physician's prescription.

After two weeks of treatment, Dale returns to the clinic for his appointment with the physician to discuss the treatment. The physician asks if Dale's skin has experienced any change in color after the treatments and examines the progress of the treatment. Dale indicates that he has not had any issues with the treatment and had not noticed any redness. Based on this information, the physician indicates that he will increase the dose of the treatment and set Dale up with another two weeks of treatment. He also informs Dale that the clinician will be able to make adjustments to the therapy thenceforth. The clinician enters the adjustments to the protocol in the Skylit Phototherapy App and proceeds to program the device.

Dale returns home and continues to use the device to treat his eczema in accordance with the prescription. At the end of the two weeks, he meets with the clinician to renew his treatment. Dale indicates that one of the sites (back of the left leg) has cleared and one of the sites (right thigh) is pink from the treatment. The clinician indicates that the treatment will be extended for another two weeks with a couple of modifications. The left leg treatment will be eliminated since clearance has been achieved. Also, the dose will be increased on all of the remaining sites except for the right thigh since that site is pink from the treatment. The next appointment with the clinician is scheduled for two weeks later.

While preferred embodiments of the present subject matter have been shown and described herein, it will be obvious to those skilled in the art that such embodiments are provided by way of example only. Numerous variations, changes, and substitutions will now occur to those skilled in the art without departing from the described subject matter. It should be understood that various alternatives to the embodiments of the subject matter described herein may be employed in practicing the subject matter described herein. It is intended that the following claims define the scope of the subject matter described herein and that methods and structures within the scope of these claims and their equivalents be covered thereby.

What is claimed is:

1. A method to guide a patient to self-administer a targeted phototherapy treatment sequence to a skin condition comprising psoriasis, eczema, or vitiligo, the method comprising:
    a) wirelessly communicating between a hand-held phototherapy device and a patient computing device to synchronize a phototherapy sequence plan to be self-administered by the patient, wherein the phototherapy sequence plan comprises a first dose of UVB light, and wherein the hand-held phototherapy device comprises an LED light source to emit the UVB light in an amount effective to treat the skin condition; and the hand-held phototherapy device is chargeable from an external power source;
    b) communicating information from the hand-held phototherapy device to the patient computing device during treatment, said information comprising a time elapsed or remaining at a treatment location;
    c) wirelessly communicating from the hand-held phototherapy device to the patient computing device confirming a treatment has been completed, or was interrupted;
    d) indicating to the patient that the hand-held phototherapy device is available for treatment at a next location, if any, using an audio or visual signal from the patient computing device or the hand-held phototherapy device; and
    e) setting a subsequent dose of the UVB light based on a patient generated self-assessment of post-treatment presence or absence of erythema observed by the patient at the treatment location using a software application; and
    f) applying the subsequent dose of the UVB light to the skin condition.

2. The method of claim 1, wherein the patient computing device is a mobile phone.

3. The method of claim 1, wherein the subsequent dose of the UVB light based on the post-treatment presence or absence of erythema at the treatment location comprises an increase in dose compared to the first dose.

4. The method of claim 1, wherein the subsequent dose of the UVB light based on the post-treatment presence or absence of erythema at the treatment location comprises a decrease in dose compared to the first dose.

5. The method of claim 1, wherein the subsequent dose of the UVB light based on the post-treatment presence or absence of erythema at the treatment location comprises the same dose compared to the first dose.

6. The method of claim 1, wherein the subsequent dose of the UVB light based on the post-treatment presence or absence is based on a preset dose adjustment method.

7. The method of claim 1, wherein the subsequent dose of the UVB light is set by the patient.

8. The method of claim 1, wherein e) comprises setting the subsequent dose of the UVB light by adjusting an amount of time of administering the UVB light.

9. The method of claim 1, wherein e) comprises setting the subsequent dose of the UVB light by adjusting an intensity of the UVB light.

10. A system for use by a patient to self-administer a targeted phototherapy treatment sequence to a skin condition comprising psoriasis, eczema, or vitiligo, the system comprising a hand-held phototherapy device comprising a phototherapy light source, and a patient computing device comprising a processor and a memory, wherein the system is configured to:
    a) wirelessly communicate between the hand-held phototherapy device and a patient computing device to synchronize a phototherapy sequence plan to be administered, wherein the phototherapy sequence plan comprises a first dose of UVB light, and wherein the hand-held phototherapy device comprises an LED light source to emit the UVB light in an amount effective to treat the skin condition; and the hand-held phototherapy device is chargeable from an external power source;
    b) communicate information from the hand-held phototherapy device to the patient computing device during treatment, said information comprising a time elapsed or remaining at a treatment location;

c) wirelessly communicate from the hand-held phototherapy device to the patient computing device when a treatment has been completed, or was interrupted; and d) indicate to the patient that hand-held phototherapy device is available for next treatment at a next location, if any, using an audio or visual cue of the patient computing device or the hand-held phototherapy device; and e) allow the patient to set a subsequent dose of the UVB light based on a patient generated self-assessment of post-treatment presence or absence of erythema observed by the patient at the treatment location using a software application.

11. The system of claim 10, wherein the patient computing device is a mobile phone.

12. The system of claim 10, wherein the LED emits light in the UVB wavelength range of 300-320 nanometers.

13. The system of claim 10, wherein the information communicated to the patient computing device includes current treatment location and time remaining on treatment.

14. The system of claim 10, wherein the patient computing device prompts a user of the patient computing device through a series of commands as to how to operate the phototherapy device during a treatment regimen.

15. The system of claim 14, wherein the system prompts the user to move to a second area of an affected site.

16. The system of claim 10, wherein the phototherapy sequence plan is wirelessly sent to the phototherapy device before initiation of treatment.

17. The system of claim 10, wherein the phototherapy sequence plan comprises instructions directing that individual sites be treated with different doses.

18. The system of claim 10, wherein the subsequent dose of the UVB light based on the post-treatment presence or absence of erythema at the treatment location comprises an increase in dose compared to the first dose.

19. The system of claim 10, wherein the subsequent dose of the UVB light based on the post-treatment presence or absence of erythema at the treatment location comprises a decrease in dose compared to the first dose.

20. The system of claim 10, wherein the subsequent dose of the UVB light based on the post-treatment presence or absence of erythema at the treatment location comprises the same dose compared to the first dose.

21. The system of claim 10, wherein the subsequent dose of the UVB light based on the post-treatment presence or absence is based on a preset dose adjustment method.

22. The system of claim 10, wherein the subsequent dose of the UVB light is set by adjusting an amount of time of administering the UVB light.

23. The system of claim 10, wherein the subsequent dose of the UVB light is set by adjusting an intensity of the UVB light.

* * * * *